United States Patent
Zhao et al.

(10) Patent No.: US 12,188,937 B2
(45) Date of Patent: Jan. 7, 2025

(54) PEPTOID COMPOUND AND DETECTION CHIP COUPLED WITH PEPTOID COMPOUND ON THE SURFACE

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zijian Zhao, Beijing (CN); Siyi Yin, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 65 days.

(21) Appl. No.: 16/977,270

(22) PCT Filed: Nov. 29, 2019

(86) PCT No.: PCT/CN2019/122007
§ 371 (c)(1),
(2) Date: Sep. 1, 2020

(87) PCT Pub. No.: WO2021/102919
PCT Pub. Date: Jun. 3, 2021

(65) Prior Publication Data
US 2023/0026155 A1 Jan. 26, 2023

(51) Int. Cl.
| | |
|---|---|
| *G01N 33/574* | (2006.01) |
| *C07C 233/36* | (2006.01) |
| *C07K 7/04* | (2006.01) |
| *C40B 40/10* | (2006.01) |
| *G01N 33/68* | (2006.01) |

(52) U.S. Cl.
CPC ..... *G01N 33/57492* (2013.01); *C07C 233/36* (2013.01)

(58) Field of Classification Search
CPC ....... G01N 33/57492; G01N 33/54386; G01N 33/54387; G01N 33/574; C07C 233/36; C07K 5/0806; C07K 5/0812
See application file for complete search history.

(56) References Cited

U.S. PATENT DOCUMENTS
| | | |
|---|---|---|
| 2019/0345198 A1 | 11/2019 | Zhao |
| 2022/0365090 A1 | 11/2022 | Zhao |

FOREIGN PATENT DOCUMENTS
| | | | |
|---|---|---|---|
| CN | 108586579 | * | 9/2018 |
| WO | 2020/140530 A1 | | 7/2020 |

OTHER PUBLICATIONS

Google Translation of CN108586579, accessed on Aug. 8, 2024.*
Extended European Search Report from European Patent Application No. 19945395.2 dated Nov. 23, 2022.
Oliver et al, "Antibody-Mimetic Peptoid Nanosheets for Molecular Recognition," ACS Nano, vol. 7, No. 10, Oct. 22, 2013, pp. 9276-9286.
Mu et al, "2D nanomaterials assembled from sequence-defined molecules," Nano-Structures & Nano-Objects, vol. 15, Jul. 2018, pp. 153-166.
Battigelli, "Design and preparation of organic nanomaterials using self-assembled peptoids," Biopolymers, vol. 10, No. 4, Feb. 23, 2019, pp. 1-13.

* cited by examiner

*Primary Examiner* — Jeanette M Lieb
*Assistant Examiner* — Erinne R Dabkowski
(74) *Attorney, Agent, or Firm* — Dilworth & Barrese, LLP.; Michael J. Musella, Esq.

(57) ABSTRACT

Embodiments disclosed herein provide a peptoid compound comprising a structure shown in Formula I and a detection chip having the peptoid compound coupled onto its surface. The peptoid compound has a strong binding ability with EpCAM protein on the surface of circulating tumor cells. The diagnostic technology of colorectal adenocarcinoma, gastric adenocarcinoma, breast cancer, ovarian cancer, lung adenocarcinoma, prostate cancer, pancreatic cancer, stem cell cancer, retinoblastoma, or primary esophageal squamous cell carcinoma based on the peptoid compound can realize rapid detection or diagnosis. In addition, the peptoid compound can be made by a simple synthesis method with high preparation efficiency and low production cost.

19 Claims, 3 Drawing Sheets

Formula I

PEPTOID COMPOUND AND DETECTION CHIP COUPLED WITH PEPTOID COMPOUND ON THE SURFACE

TECHNICAL FIELD

The embodiments disclosed herein relate to a peptoid compound and a detection chip coupled with the peptoid compound on the surface.

BACKGROUND

Epithelial cell adhesion molecule (EpCAM) belongs to the family of adhesion molecules. It is a single transmembrane protein encoded by a tumor-associated calcium signal transducer 1 (TACSTD1) gene, and is involved in regulating cell-to-cell adhesion, and mediates signal transduction, cell migration, proliferation, and differentiation. Under pathological conditions, EpCAM is expressed in almost all adenocarcinomas, including colorectal adenocarcinoma, gastric adenocarcinoma, breast cancer, ovarian cancer, lung adenocarcinoma, prostate cancer, pancreatic cancer, as well as stem cell cancer and retinoblastoma. EpCAM activates the expression of protooncogenes such as c-myc gene and cyclin A/E by participating in a β-catenin-dependent Wnt cascade, thereby having tumorigenic effects. At the same time, EpCAM is also an important indicator of tumor prognosis. Under normal circumstances, EpCAM is negatively expressed in esophageal squamous epithelium. However, in primary esophageal squamous cell carcinoma, almost 80% of tumors express EpCAM at various degrees. The average interval of postoperative recurrence of EpCAM-strongly positive esophageal squamous cell carcinoma is 9 months, while the average interval of postoperative recurrence of EpCAM-negative, weakly positive, and positive esophageal squamous cell carcinoma is 43 months, indicating that the overexpression of EpCAM affects the prognosis of esophageal squamous cell carcinoma. In addition, the overexpression of EpCAM in breast cancer and gastric cancer, etc. is also an important indicator of cancer cell metastasis.

Due to the heterogeneity of tumors, taking the tumor tissue just from a certain part is not enough to reflect the overall condition of the patient whose cancer cells have metastasized. However, it is impractical to sample all tumor tissues in the patient. Therefore, the tissue biopsy technique has certain limitations. Liquid biopsy technology does not need to take the tumor tissue from the patient, but only needs to take the patient's blood or secretions for testing. Therefore, liquid biopsy technology draws more and more attention of researchers and research on liquid biopsy technology is growing. Liquid biopsy technology includes using peptoid compounds to detect circulating tumor cells (CTC), circulating tumor DNA (ctDNA) and exosomes, etc.

Circulating tumor cell (CTC) is a collective name for various types of tumor cells that exist in peripheral blood. It is detached from solid tumor lesions (primary lesions, metastases) spontaneously or due to diagnosis or treatment operation. Most CTCs undergo apoptosis or are swallowed after entering the peripheral blood. A few can escape and develop into metastases, increasing the risk of death in patients with malignant tumors. The presence or absence of CTC and the amount of CTC are important indicators of cancer progression and metastasis. Detection and tracking of the amount of CTCs in peripheral blood is helpful for early screening, efficacy monitoring, prognostic judgment and recurrence prediction of patients.

The detection technology for CTC can predict the occurrence of early tumors, and can detect the tumor metastasis during treating patients with drugs. In addition, it can also guide medication for subsequent treatment. CTC are derived from primary tumors or metastatic tumors. CTC can enter blood vessels after being detached from basement membrane. Because the content of CTC in the blood is extremely low and its size is similar to the size of white blood cells, CTC are difficult to be detected using liquid biopsy technology. However, CTC carry relevant cancer-specific, highly expressed proteins on their surfaces.

In an early stage of cancer development, CTC screening technology can be used to diagnose cancers. CTC screening detection needs to capture circulating tumor cells from the blood. The detection process is closely related to probe molecules coupled to a surface of a capture device, and specific capture is achieved through the affinity of the probe molecules and CTC surface proteins. Antibodies, as probe molecules, have the characteristics of tightly binding to biosensors. However, the arrangement of antibody molecules is disordered. The arrangement of antibody molecules on the sensor surface is random in direction and difficult to be controlled, resulting in low specificity. Moreover, the cost of antibodies is high. Therefore, it is necessary to develop a new probe molecule for CTC screening detection or diagnosis of cancers.

SUMMARY

At least one embodiment disclosed herein provides a peptoid compound comprising a structure as shown in Formula I, and the peptoid compound includes 1,4-butanediamine subunit, 2-(4-biphenylyl)ethylamine subunit, 3-aminopropionic acid subunit, and phenethylamine subunit

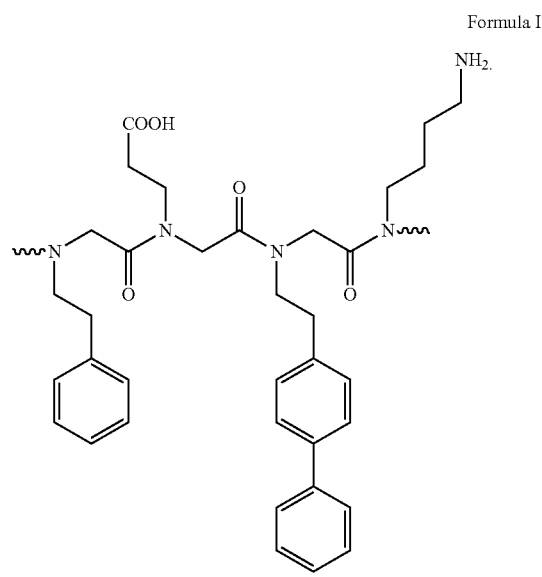

Formula I

In one embodiment, in the peptoid compound provided in at least one example disclosed herein, the peptoid compound has a molecular structural formula of:

Formula II

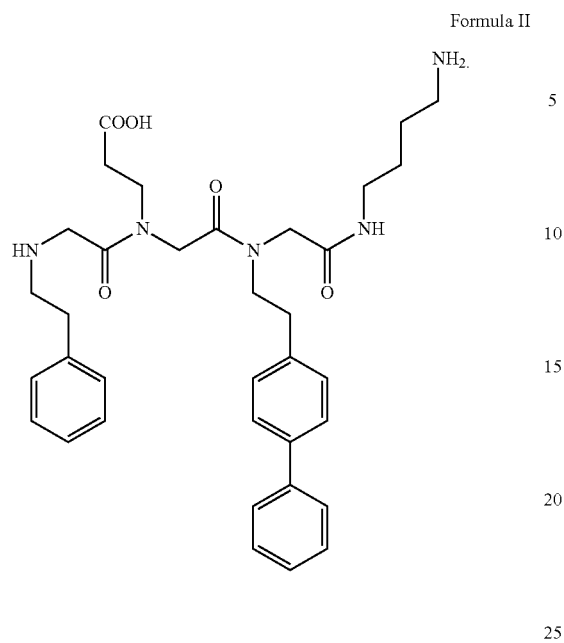

In another embodiment, in the peptoid compound provided in at least one example disclosed herein, the peptoid compound has 30 to 100 subunits. For example, in the peptoid compound provided in at least one example disclosed herein, the structure shown in Formula I is not located at the two ends of the structure of the peptoid compound.

For example, in the peptoid compound provided in at least one example disclosed herein, the peptoid compound has a molecular structural formula of:

Formula III

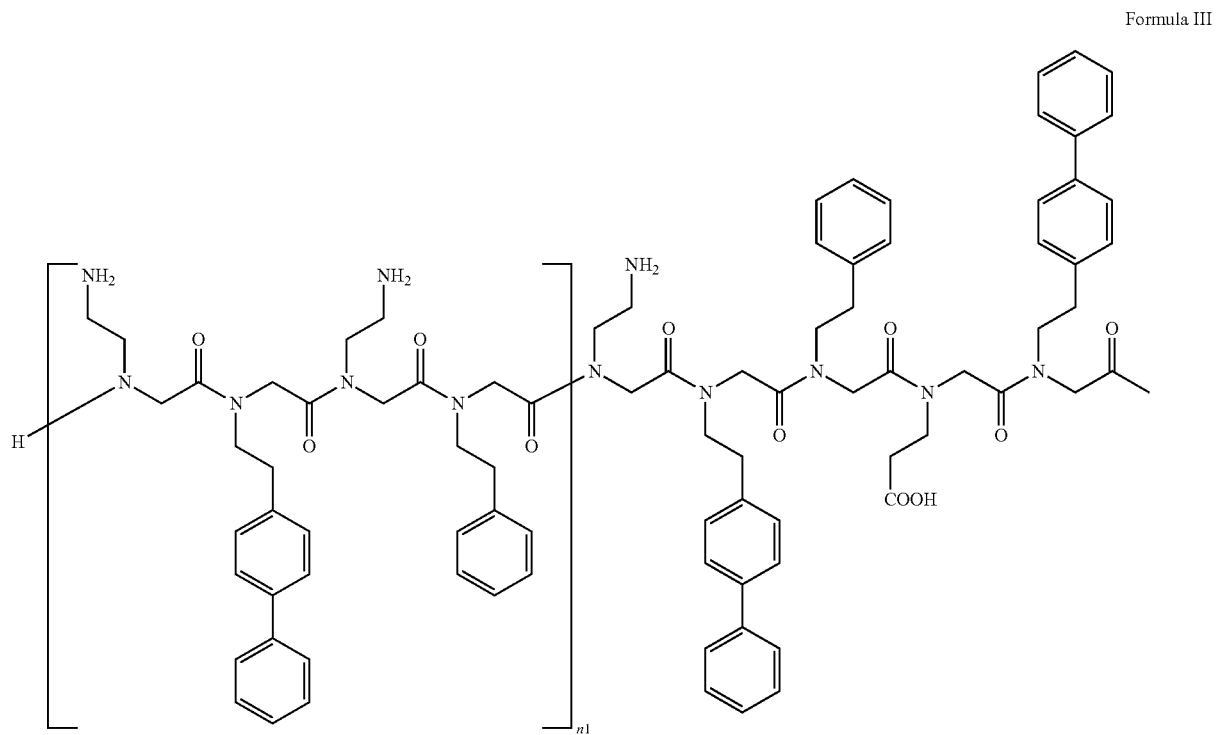

-continued

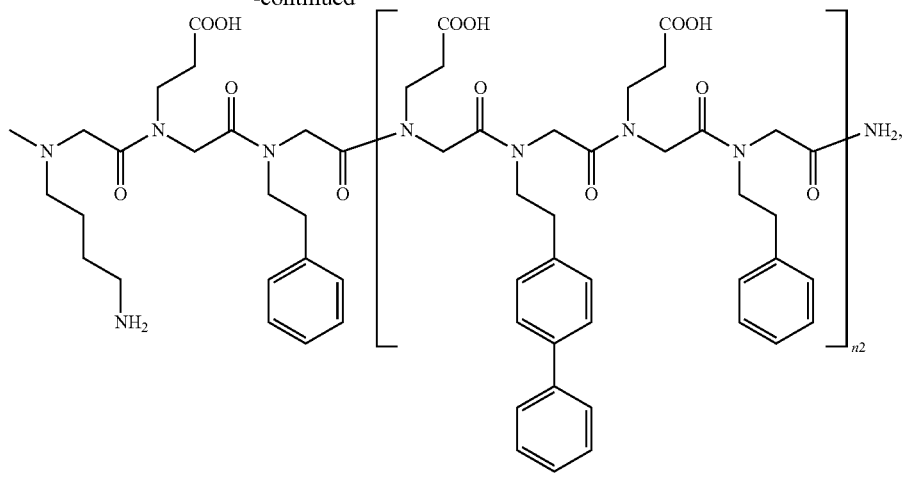

wherein n1 is greater than or equal to 3 and less than or equal to 10; n2 is greater than or equal to 3 and less than or equal to 10; and n1 and n2 are both natural numbers. For example, in one embodiment, n1 is equal to n2. In a preferred embodiment, n1 is equal to n2, and n1 is 3, 5 or 7.

For example, in the peptoid compound provided in at least one example disclosed herein, the peptoid compound has a molecular structural formula of:

Formula IV

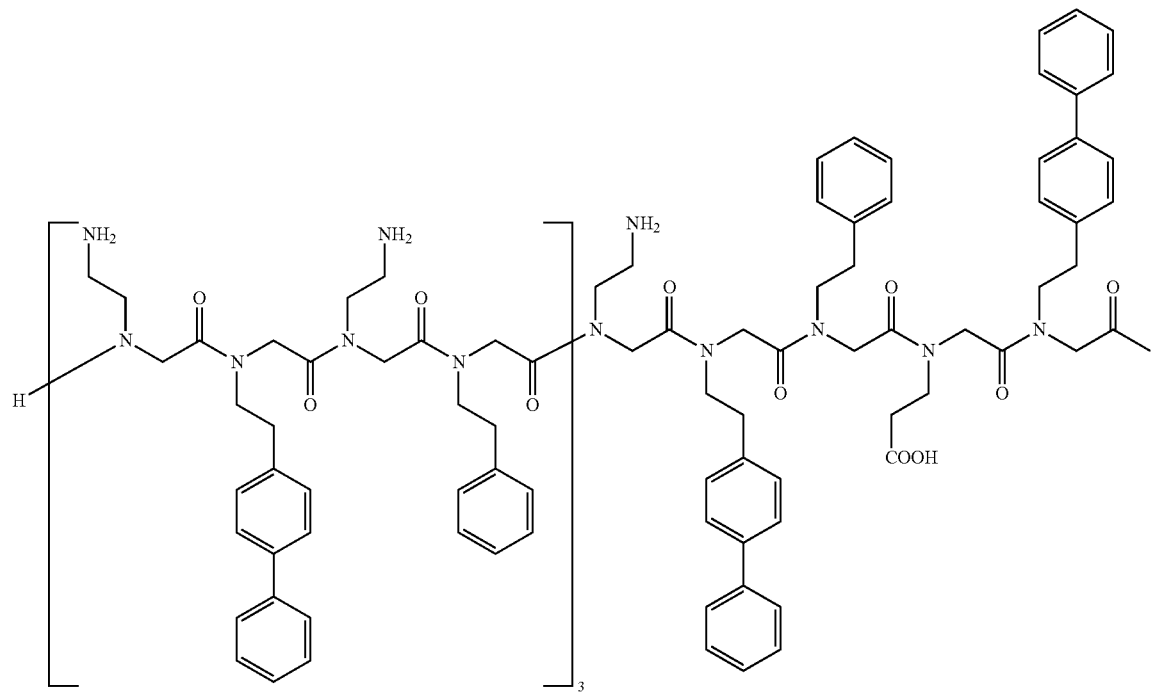

-continued

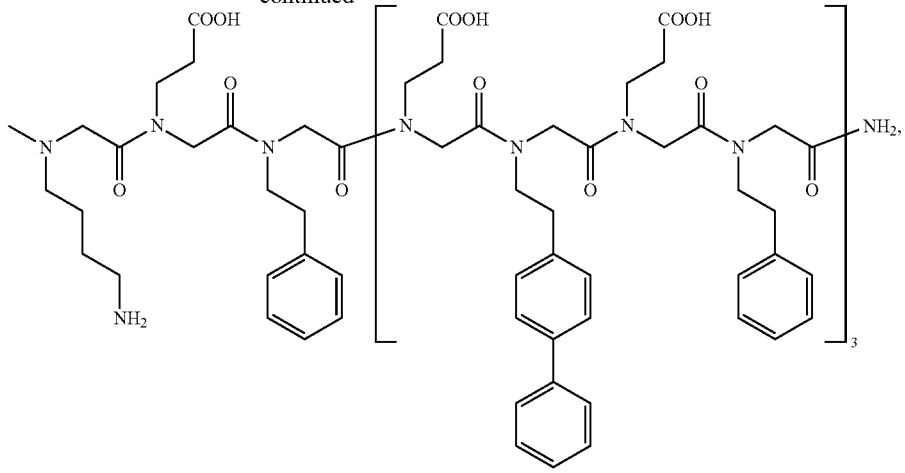

At least one embodiment disclosed herein also provides a detection chip, the surface of which is coupled with any of the aforementioned peptoid compounds. In one embodiment, the peptoid compound coupled to the surface of the chip is the peptoid compound represented by Formula III, preferably the peptoid compound represented by Formula IV.

In a preferred embodiment, the detection chip is a microfluidic chip.

In one embodiment, the aforementioned chip can be useful in detecting or diagnosing a disease associated with EpCAM protein. For example, the disease includes colorectal adenocarcinoma, gastric adenocarcinoma, breast cancer, ovarian cancer, lung adenocarcinoma, prostate cancer, pancreatic cancer, stem cell cancer, retinoblastoma, or primary esophageal squamous cell carcinoma.

BRIEF DESCRIPTION OF THE DRAWINGS

In order to explain the technical solutions of embodiments disclosed herein more clearly, the drawings of the embodiments will be briefly introduced. Apparently, the drawings in the following description only relate to some examples disclosed herein, rather than limit the present invention.

DETAILED DESCRIPTION

Figure 1:
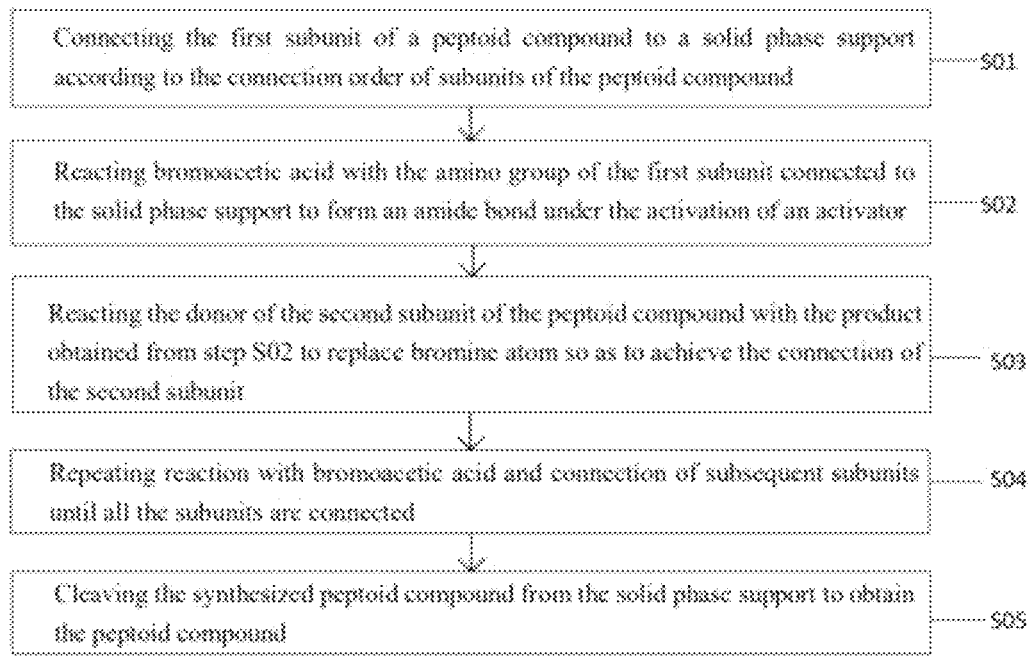
FIG. 1 is a flow chart of a method for preparing a peptoid compound according to an example disclosed herein.

To make the objectives, technical solutions, and advantages of embodiments disclosed herein more clearly, the technical solutions of embodiments disclosed herein will be described clearly and completely in conjunction with the accompanying drawings. Apparently, the described embodiments are part of the embodiments disclosed herein, rather than all of the embodiments. Based on the described embodiments disclosed herein, all other embodiments obtained by those of ordinary skill in the art without creative labor are within the protection scope of the present invention.

The various documents and publications mentioned in this disclosure are incorporated herein by reference. Unless otherwise defined, the technical or scientific terms used in this disclosure shall have the ordinary meaning as understood by those of ordinary skill in the art to which this invention belongs. The word "including", "containing", "comprising", or the like indicates that the element appearing before the word encompasses the element listed after the word and its equivalent, without excluding other elements.

The peptoid compounds disclosed herein include peptoid small molecules and peptoid macromolecules, wherein the peptoid small molecules have less than 10 subunits, and the peptoid macromolecules have more than 10 subunits, for example, 10 to 100 subunits.

The experimental methods used in the following examples are conventional methods unless otherwise specified. The materials and reagents used in the following examples can be obtained from commercial sources unless otherwise specified. For example, the EpCAM protein was purchased from Sino Biological Inc. in Beijing.

The SPRi instrument in the following examples is Plexera Kx5V2 from Plexera Bioscience LLC, USA. The instrument is mainly equipped with a 660 nm LED light source, a CCD image collector and a sensor chip with a microfluidic channel. The instrument displays the change in the intensity of the reflected light at each monitoring point over time and records it as a SPR curve.

Unless otherwise specified, "nM" as used herein refers to "nmol/L", and "mM" refers to "mmol/L".

The detection technology for CTC can predict the occurrence of early tumors, and can detect the tumor metastasis during treating patients with drugs. In addition, it can also guide medication for subsequent treatment. CTC is derived from primary tumors or metastatic tumors. CTC can enter blood vessels after being detached from basement membrane. Because the content of CTC in the blood is extremely low and its size is similar to the size of white blood cells, CTC is difficult to be detected using liquid biopsy technology. However, CTC carries relevant cancer-specific, highly expressed proteins on its surface. For example, under pathological conditions, EpCAM is commonly expressed in colorectal adenocarcinoma, gastric adenocarcinoma, breast cancer, ovarian cancer, lung adenocarcinoma, prostate cancer, pancreatic cancer, stem cell cancer and retinoblastoma. Therefore, by specifically identifying the EpCAM protein on the CTC surface of colorectal adenocarcinoma, gastric adenocarcinoma, breast cancer, ovarian cancer, lung adenocarcinoma, prostate cancer, pancreatic cancer, stem cell cancer and retinoblastoma patients with high expression of EpCAM, a favorable guarantee is provided for capturing the corresponding CTC with high sensitivity. For example, molecular probes with high affinity and sensitivity to EpCAM protein can be designed.

Polypeptides use alpha amino acids as structural units, whereas peptoids are polypeptide mimics with N-substituted glycine as structural units. Compared with a polypeptide, side chains of a peptoid are transferred from α-carbon to nitrogen. Different from traditional polypeptides which are composed of only 20 kinds of amino acids, the peptoid is synthesized by a monomer synthesis process and its constituent units are determined by different amines. There are thousands of amines, and thus the peptoids have extremely abundant sequences. It is possible to develop different chemical sequence structures for different targets. Because the peptoids are not recognized by enzymes, the peptoids can effectively resist proteolysis in vivo, which makes the peptoids have more significant advantages as a molecular probe.

Small peptoid molecules have the characteristics of low immunogenicity, good tissue permeability, small molecular weight, high stability, easy modification and low manufacturing cost. Antibodies have the characteristic of tightly binding to biosensors. However, the arrangement of antibody molecules is disordered. The arrangement of antibody molecules on the sensor surface is random in direction and difficult to be controlled, resulting in low specificity. Moreover, the cost of antibodies is higher.

The inventors of the present disclosure have discovered that peptoid macromolecules with 30 to 100 subunits can well combine the characteristics of peptoid small molecules and antibodies, that is, such peptoid macromolecules not only have the characteristic of antibodies regarding tight binding to biosensors, but also can be formed on the surface of sensors in an orderly manner like small peptoid molecules. In addition, compared with small peptoid molecules, molecular probes formed with the peptoid macromolecules have stronger affinity with tumor cells. Moreover, such peptoid macromolecules are less likely to be digested by enzymes, which can ensure the activity of natural living samples.

At least one embodiment disclosed herein provides a peptoid compound, which includes 1,4-butanediamine subunit, 2-(4-biphenylyl)ethylamine subunit, 3-aminopropionic acid subunit, and β-phenethylamine subunit. Respective subunit is derived from the following subunit donor:

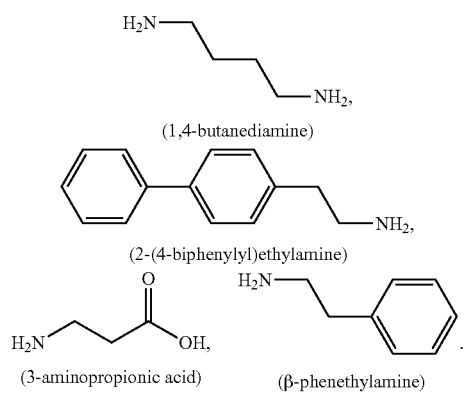

For example, in the peptoid compound provided in at least one example disclosed herein, the peptoid compound has a structure shown in Formula I:

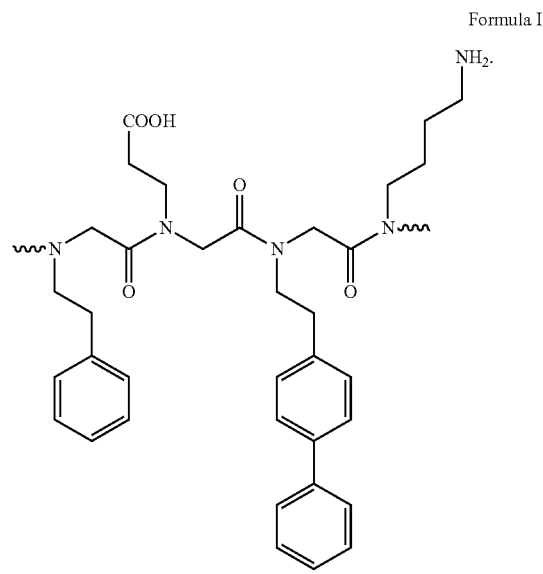

Formula I

In one embodiment, the peptoid compound is a peptoid small molecule with 4 subunits, that is, has a structural formula of

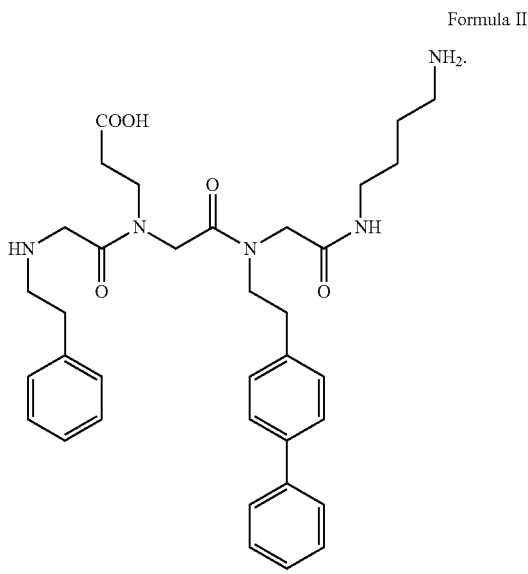 [SMILES: NCCCCNC(=O)CN(CCc1ccc(-c2ccccc2)cc1)C(=O)CN(CCC(=O)O)C(=O)CNCCc1ccccc1]

Formula II

In one embodiment, the peptoid compound is a peptoid macromolecule with 30 to 100 subunits. Preferably, the structure shown in Formula I is not located at the two ends of the structure of the peptoid macromolecule. For example, the peptoid compound has a molecular structure formula of
Formula III
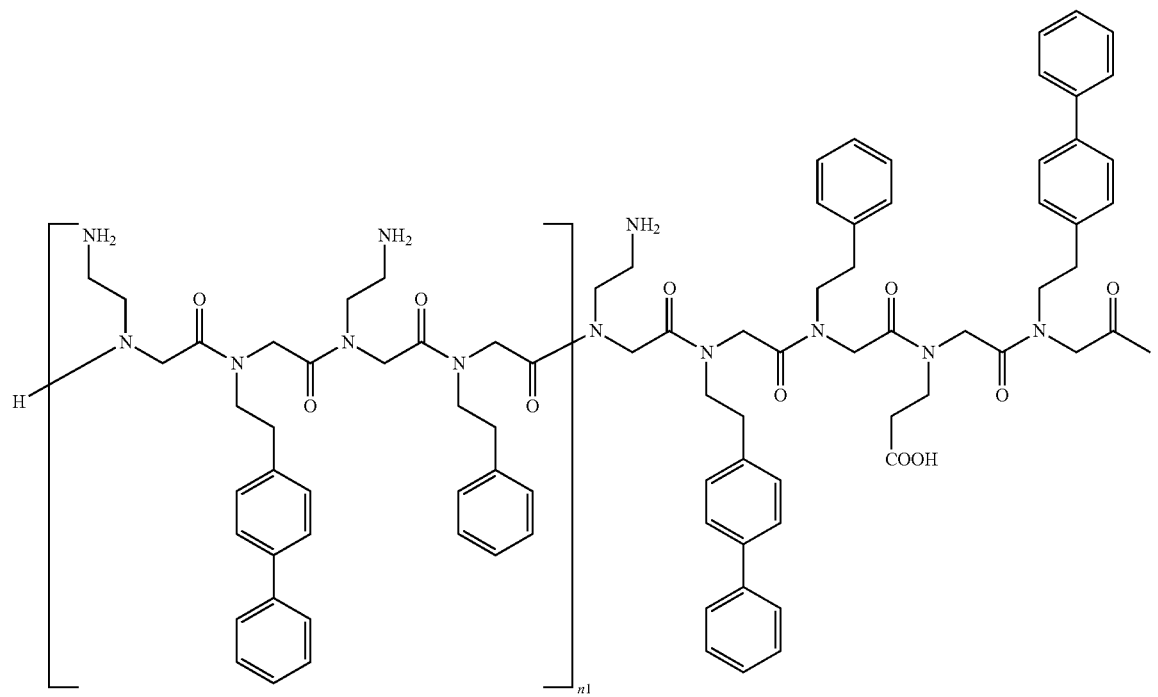
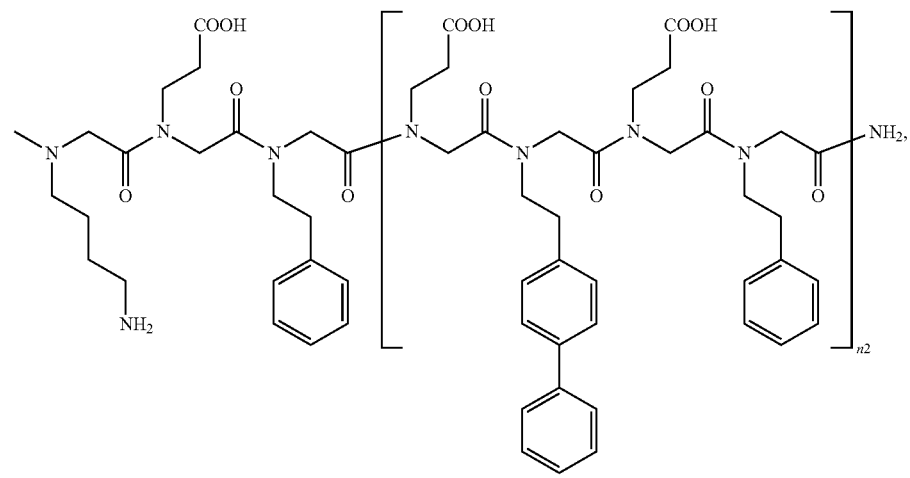

wherein n1 is greater than or equal to 3 and less than or equal to 10; n2 is greater than or equal to 3 and less than or equal to 10; and n1 and n2 are both natural numbers. In a preferred embodiment, n1 is equal to n2. For example, n1 is equal to n2, and n1 is 3, 5, or 7. In a more preferred embodiment, the peptoid compound has a molecular structural formula of:

The peptoid compound disclosed herein can be synthesized by the solid phase synthesis method as shown below. The solid phase synthesis method is well known to those skilled in the art. For example, a solid phase synthesis method of peptoids is reported in J. Am. Chem. Soc. 1992, 114, 10646-10647.

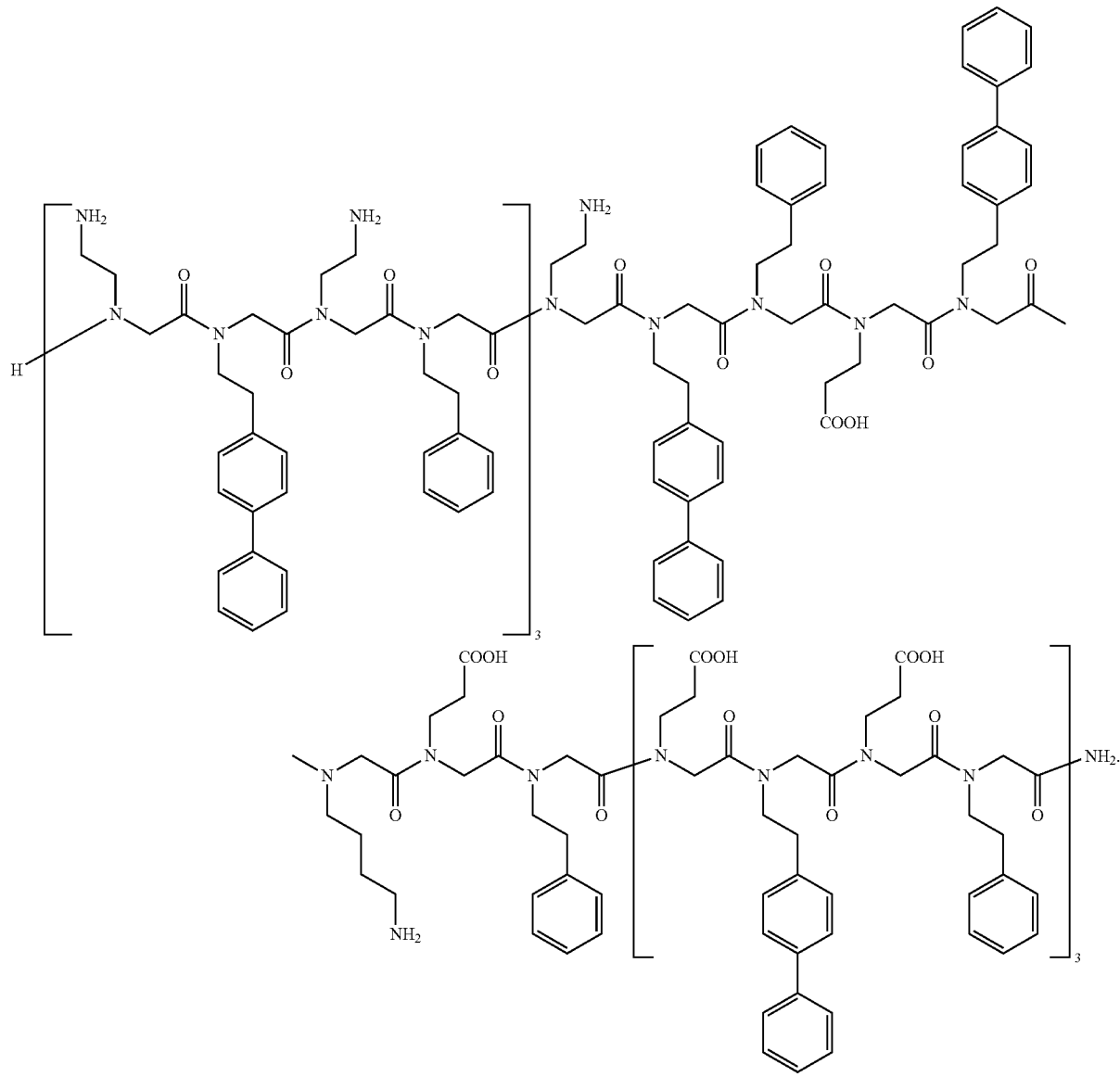

Formula IV

The aforementioned peptoid compounds can be used as probe molecules to specifically identify EpCAM protein. That is, the peptoid compounds can bind to EpCAM protein, a marker of colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma, and can be used to detect colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma.

Reaction equation 1

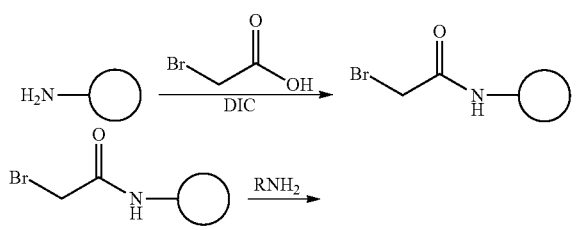

-continued $$\underset{H}{\overset{R}{N}}\underset{}{\overset{}{\bigvee}}\underset{H}{\overset{O}{N}}\bigcirc$$

In the above reaction equation 1, bromoacetic acid may be replaced with bromoacetyl chloride.

At least one embodiment disclosed herein also provides a method for preparing the peptoid compound. For example, FIG. 1 is a flow chart of a preparation method of a peptoid compound provided in an example disclosed herein. As shown in FIG. 1, the preparation method includes the following steps:

Step S01: connecting the first subunit of a peptoid compound to a solid phase support according to the connection order of subunits of the peptoid compound;

Step S02: reacting bromoacetic acid with the amino group of the first subunit connected to the solid phase support to form an amide bond under activation of an activator;

Step S03: reacting the donor of the second subunit of the peptoid compound with the product obtained from step S02 to replace bromine atom to complete the connection of the second subunit;

Step S04: repeating reacting with bromoacetic acid and subsequent subunit connection until the connection of all subunits is completed;

Step S05: cleaving the synthesized peptoid compound from the solid phase support to obtain the peptoid compound.

The donor of subunit refers to a compound offering a subunit of a peptoid. For example, the donor of 1,4-butanediamine subunit is 1,4-butanediamine, the donor of 2-(4-biphenylyl)ethylamine subunit is 2-(4-biphenylyl)ethylamine, the donor of 3-aminopropionic acid subunit is 3-aminopropionic acid, and the donor of 0-phenethylamine subunit is β-phenethylamine.

As an amino-protecting group, amino-protecting groups known in the art for the synthesis of proteins, polypeptides, or peptoids can be used without limitation, for example, amino protecting groups listed in Greene's Protective Groups in Organic Synthesis, 5th edition by Peter G. M. Wuts. In some embodiments, the amino protecting group is 9-fluorenylmethoxycarbonyl (Fmoc) or tert-butoxycarbonyl (Boc). For example, in some embodiments, the amino protecting group is tert-butoxycarbonyl. For example, Boc protected butanediamine is used as a donor of 1,4-butanediamine subunit.

The removal of the side chain amino protecting group and the cleavage of the peptoid from the resin can use conventional conditions in the art for synthesizing protein, polypeptide or peptoid, as long as the purpose can be achieved without disrupting the function of the peptoid. In one embodiment, a lysate containing 95% trifluoroacetic acid, 2.5% ultrapure water, and 2.5% triisopropylsilane in volume ratio can be used to remove the side chain amino protecting group while cleaving the peptoid from the resin.

For example, in order to prepare the peptoid small molecule of Formula II, the input order of subunit donors is, for example, Boc-protected butanediamine, 2-(4-biphenylyl)ethylamine, 3-aminopropionic acid and β-phenethylamine.

For example, the solid phase support is Rink amide AM resin.

For example, before connecting the first subunit of the peptoid to the solid phase support, the solid phase support is swollen.

For example, when the solid phase support is Rink amide AM resin, it is swollen and deprotected with hexahydropyridine to expose the amino group of Rink amide AM resin.

For example, the process of connecting the first subunit of the peptoid to the solid phase support is carried out under the action of a condensing agent and an activator.

For example, the condensing agent is any one or a combination of at least two of 2-(3'-N-oxo-benzotriazol)-1,1',3,3'-tetramethylurea hexafluorophosphate, O-benzotriazol-N,N,N',N'-tetramethylurea tetrafluoroborate, or 1-hydroxybenzotriazole.

For example, the activator used in step S01 is N-methylmorpholine.

For example, the activator used in step S02 is N,N'-diisopropylcarbodiimide (DIC) or dicyclohexylcarbodiimide.

For example, the reaction temperature in step S02 is 20-40° C., such as 20° C., 21° C., 23° C., 24° C., 25° C., 33° C., 34° C., 36° C., 38° C. or 40° C.

For example, the reaction time in step S02 is 10-100 min, such as 10 min, 15 min, 20 min, 25 min, 30 min, 35 min, 40 min, 50 min, 60 min, 70 min, 80 min, 90 min or 100 min.

For example, the reaction temperature in step S03 is 20-40° C., such as 20° C., 21° C., 23° C., 24° C., 25° C., 33° C., 34° C., 36° C., 38° C. or 40° C.

For example, the reaction time in step S03 is 30-180 min, such as 30 min, 35 min, 45 min, 50 min, 55 min, 60 min, 65 min, 70 min, 80 min, 90 min, 100 min, 120 min, 140 min, 150 min, 160 min, 170 min or 180 min.

For example, in step S04, reacting with bromoacetic acid and subsequent subunit connection is repeated, that is, steps S04 and S03 are repeated, with the only exception that the connected subunit is the subsequent subunit.

For example, the cleaving agent used for cleaving in step S05 includes the following components: 95 wt % trifluoroacetic acid, 2.5 wt % ultrapure water and 2.5 wt % triisopropylsilane.

For example, in the preparation process of peptoid compounds, groups that do not participate in the connection reaction can be protected to ensure the accuracy of the connection site, so that the reaction proceeds more accurately and smoothly. After the connection of all the subunits is completed, deprotection is carried out to remove the protecting group.

For example, the synthesis of peptoids by solid phase subunit synthesis method specifically includes the following steps:

(1) a Rink amide AM resin (the level of substitution is 0.3 mmol/g) is swollen, and then deprotected with hexahydropyridine; and cysteine is mixed equimolarly with 2-(3'-N-oxo-benzotriazol)-1,1',3,3'-tetramethylurea hexafluorophosphate and coupled under the activation of N-methylmorpholine;

(2) 10 mL of bromoacetic acid with a concentration of 2 mol/L and 10 mL of N,N'-diisopropylcarbodiimide (DIC) with a concentration of 3.2 mol/L are added into the Rink amide AM resin (starting resin for polypeptide synthesis, the level of substitution is 0.3 mmol/g), and reacted at 37° C. for 30 minutes to acylate the amino group at the end of the resin;

(3) 10 mL of 2 mol/L primary amine is then added and reacted at 37° C. for 90 min so as to replace the bromine atom by nucleophilic substitution reaction to complete the synthesis of one subunit;

(4) steps (2) and (3) are repeated until the synthesis of remaining subunits is completed; and (5) after the synthesis is completed, the side chain protecting group is removed, and the peptoid compound is cleaved from the resin with a cleaving agent including 95 wt % trifluoroacetic acid, 2.5 wt % ultrapure water and 2.5 wt % triisopropylsilane.

For example, in the preparation method of the peptoid compound provided in the example disclosed herein, the step of purifying the obtained product may also be included as needed. The purification method is not particularly limited, and methods known in the art for purifying corresponding similar products, such as precipitation, filtration, dialysis, and gel permeation chromatography can be used.

At least one embodiment disclosed herein also provides a peptoid macromolecule with a molecular structural formula of:

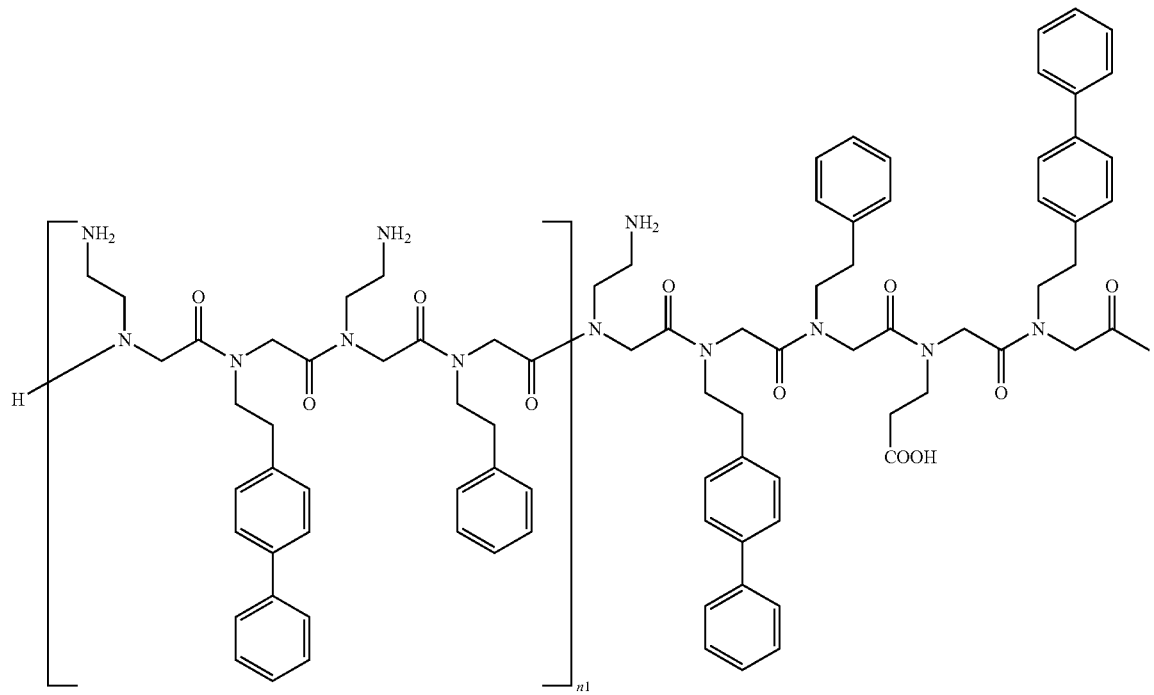

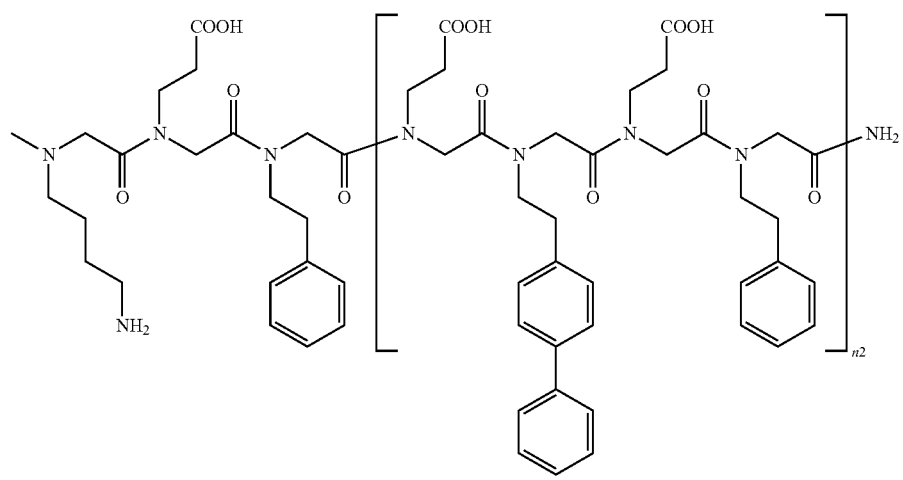

wherein n1 is greater than or equal to 3 and less than or equal to 10; n2 is greater than or equal to 3 and less than or equal to 10; and n1 and n2 are both natural numbers.

For example, subunit donors have the molecular structural formulae as shown below:

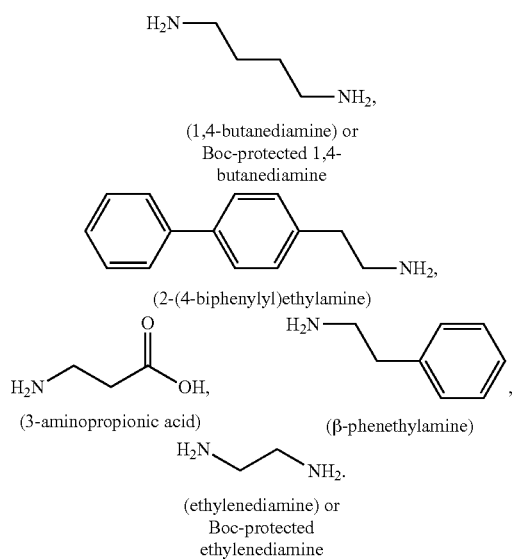

(1,4-butanediamine) or Boc-protected 1,4-butanediamine (2-(4-biphenylyl)ethylamine)

(3-aminopropionic acid)

(β-phenethylamine)

(ethylenediamine) or Boc-protected ethylenediamine

For example, in a peptoid macromolecule provided by at least one embodiment disclosed herein, the subunits contained in the peptoid macromolecule are arranged in the following order: [β-phenethylamine subunit-3-aminopropionic acid subunit-2-(4-biphenylyl)ethylamine subunit-3-aminopropionic acid subunit]$_{n2}$-β-phenethylamine subunit-3-aminopropionic acid subunit-1,4-butanediamine subunit-2-(4-biphenylyl)ethylamine subunit-3-aminopropionic acid subunit-β-phenethylamine subunit-2-(4-biphenylyl)ethylamine subunit-ethylenediamine subunit-[β-phenethylamine subunit-ethylenediamine subunit-2-(4-biphenylyl)ethylamine subunit-ethylenediamine subunit]$_{n1}$.

At least one embodiment disclosed herein also provides a method for preparing a peptoid macromolecule. The peptoid macromolecule is also synthesized by a solid phase subunit synthesis method. It differs from the preparation of the peptoid small molecule of Formula II in the input order of subunit donors.

For example, the peptoid macromolecule includes the peptoid small molecule structure of Formula I and helper chains formed on its left and right sides. The helper chain on the left side contains amino groups, and the helper chain on the right side contains carboxyl groups. The helper chain helps the peptoid macromolecule to form a two-dimensional layered structure, so that the middle peptoid structure can be exposed on the surface of a sensor as a probe molecule to detect EpCAM proteins. The helper chain can also make the arrangement of the peptoid macromolecules orderly.

For example, the condensing agent and activator used in each step of the preparation process of the peptoid macromolecule can refer to the relevant description of the preparation process of the aforementioned peptoid compound, which will not be repeated here.

For example, in the peptoid macromolecule, both of n1 and n2 are 3, 4, 5, 6, 7, 8, 9, or 10 (i.e., n1=n2=3, n1=n2=4, n1=n2=5, n1=n2=6, n1=n2=7, n1=n2=8, n1=n2=9, or n1=n2=10).

It should be noted that when n1 and n2 are less than 3, there will be a problem that the chain length is too short to be assembled; when n1 and n2 are greater than 10, the formed chain is too long, and the density of the peptoid small molecule structure of Formula I inserted in the middle of the peptoid macromolecule is too low, resulting in a weakened affinity and a failure of specific binding to EpCAM proteins on the CTC.

Example 1

The molecular structure of Formula IV is:

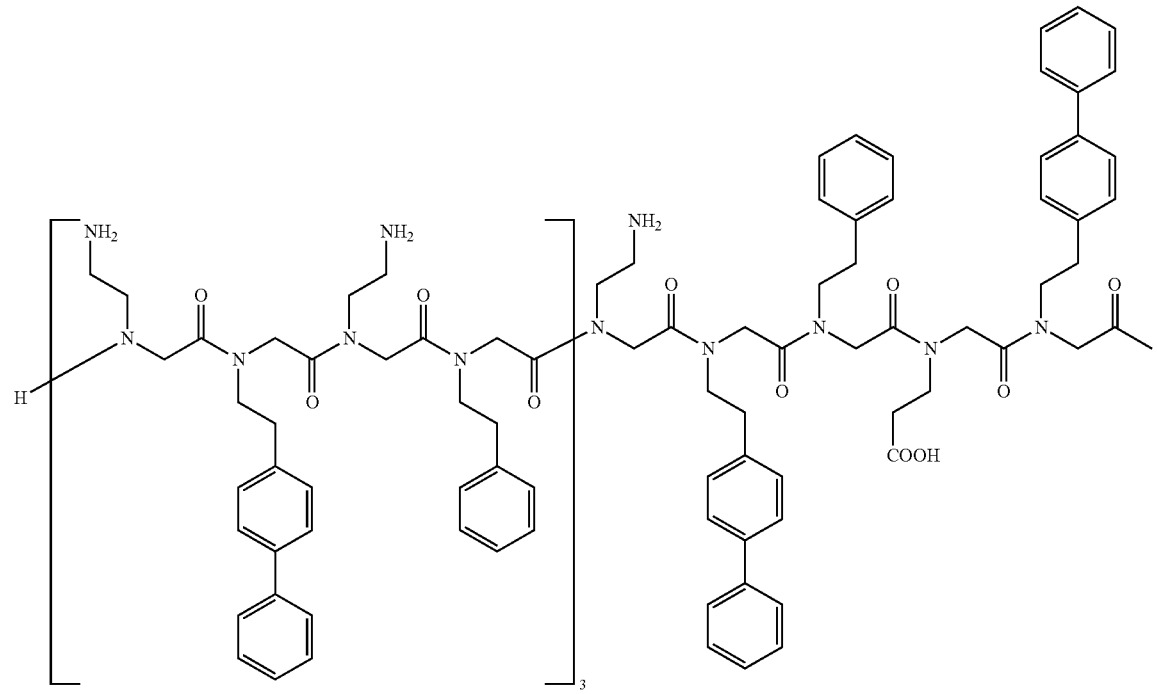

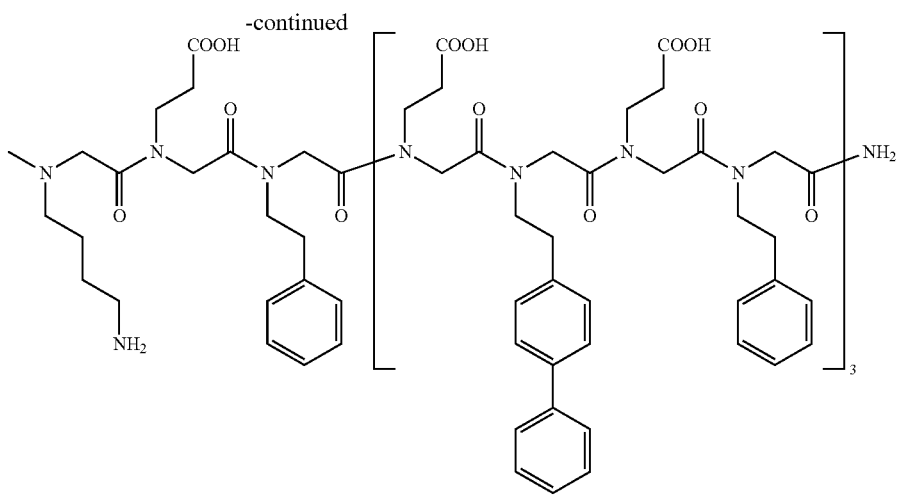

-continued

The preparation method of the peptoid macromolecule of Formula IV specifically includes the following steps:

(1) a Rink amide AM resin (starting resin for polypeptide synthesis, the level of substitution was 0.3 mmol/g) was swollen, and then deprotected with hexahydropyridine; and β-phenethylamine was mixed equimolarly with 1-hydroxybenzotriazole and coupled under the activation of N-methylmorpholine;

(2) 10 mL of bromoacetic acid with a concentration of 2 mol/L and 10 mL of N,N'-diisopropylcarbodiimide (DIC) with a concentration of 3.2 mol/L were added into the Rink amide AM resin, and reacted at 38° C. for 30 minutes to acylate the amino group at the end of the resin;

(3) 2 mol/L primary amine was added and reacted at 37° C. for 90 min so as to replace the bromine atom by nucleophilic substitution reaction to complete the synthesis of one subunit;

(4) steps (2) and (3) were repeated until the synthesis of remaining subunits was completed; and (5) after the synthesis was completed, the side chain protecting group was removed, and the peptoid macromolecule was cleaved from the resin with a cleaving agent including 95 wt % trifluoroacetic acid, 2.5 wt % ultrapure water and 2.5 wt % triisopropylsilane.

In the process of forming the peptoid macromolecule of the above structure, the input order of subunit donors is:

β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-Boc-protected 1,4-butanediamine-2-(4-biphenylyl)ethylamine-3-aminopropionic acid-β-phenethylamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine.

For example, the peptoid macromolecule can be dissolved in a mixed solution of dimethyl sulfoxide (DMSO) and water ($H_2O$) with a molar ratio of 2:1 (dimethyl sulfoxide:water) to obtain a concentration of 2 mM.

Example 2

The molecular structure is:

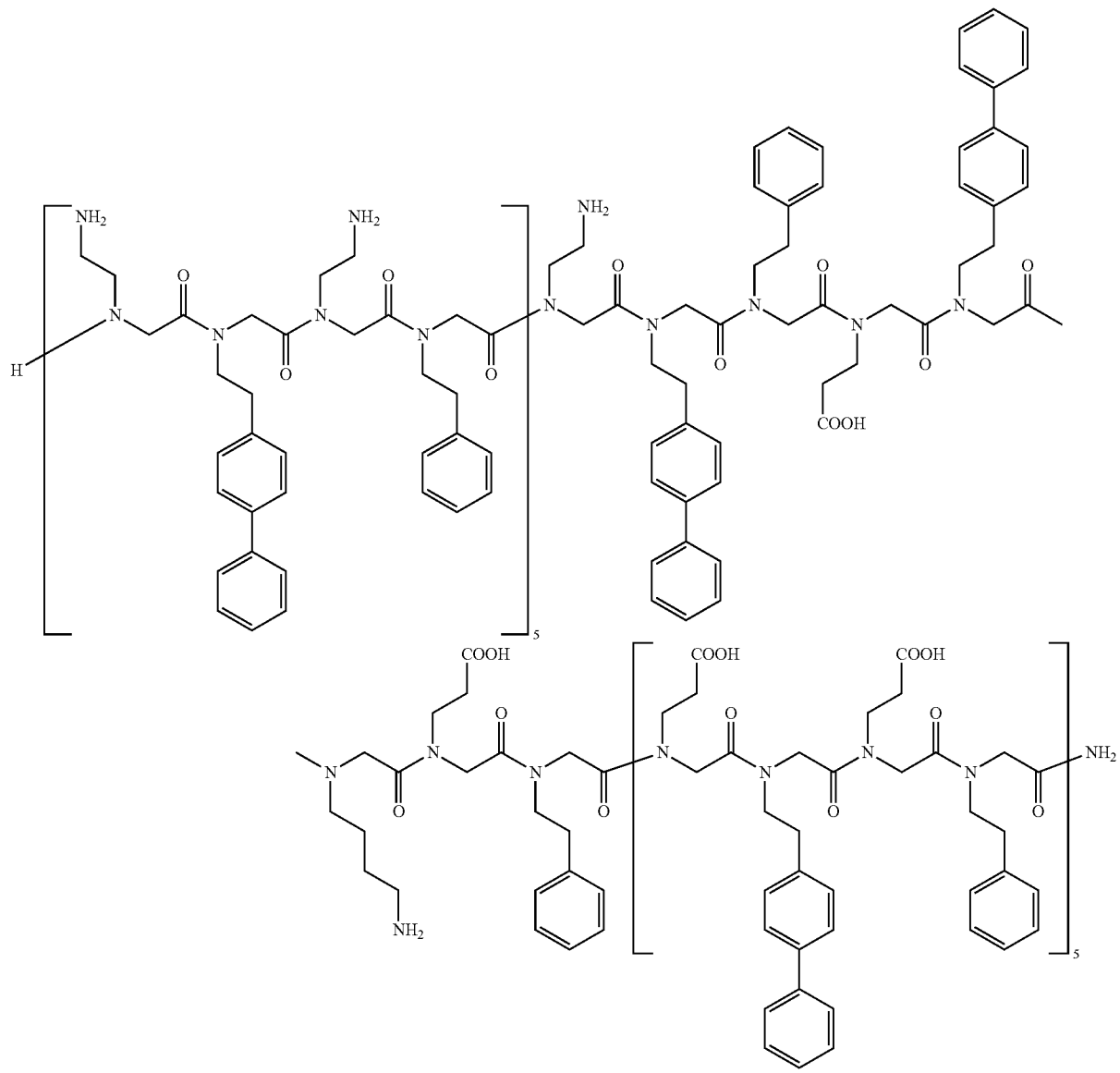

The preparation method of the peptoid macromolecule specifically includes the following steps:

(1) a Rink amide AM resin (starting resin for polypeptide synthesis, the level of substitution was 0.3 mmol/g) was swollen, and then deprotected with hexahydropyridine; and β-phenethylamine was mixed equimolarly with 1-hydroxybenzotriazole and coupled under the activation of N-methylmorpholine;

(2) 20 mL of bromoacetic acid with a concentration of 2 mol/L and 15 mL of N,N'-diisopropylcarbodiimide (DIC) with a concentration of 3.2 mol/L were added into the Rink amide AM resin, and reacted at 38° C. for 30 minutes to acylate the amino group at the end of the resin;

(3) 2 mol/L primary amine was added and reacted at 37° C. for 90 min so as to replace the bromine atom by nucleophilic substitution reaction to complete the synthesis of one subunit;

(4) steps (2) and (3) were repeated until the synthesis of remaining subunits was completed; and (5) after the synthesis was completed, the side chain protecting group was removed, and the peptoid macromolecule was cleaved from the resin with a cleaving agent including 95 wt % trifluoroacetic acid, 2.5 wt % ultrapure water and 2.5 wt % triisopropylsilane.

For example, in the process of forming the peptoid macromolecule of the above structure, the input order of subunit donors is:

β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-Boc-protected 1,4-butanediamine-2-(4-biphenylyl)ethylamine-3-aminopropionic acid-β-phenethylamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine.

For example, the peptoid macromolecule can be dissolved in a mixed solution of dimethyl sulfoxide (DMSO) and water ($H_2O$) with a molar ratio of 2:1 (dimethyl sulfoxide:water) to obtain a concentration of 2 mM.

Example 3

The molecular structure is:

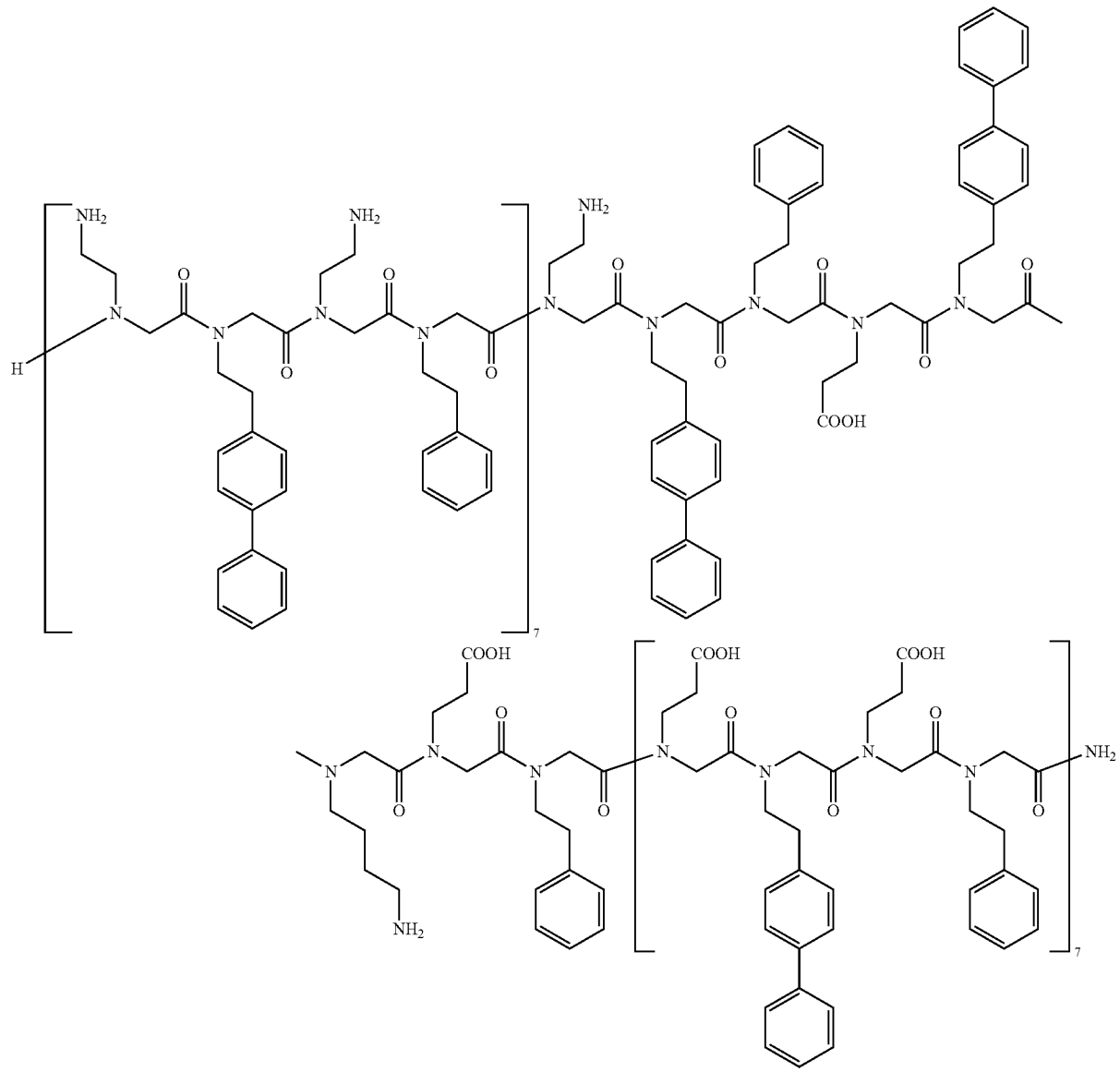

tected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl) ethylamine-Boc-protected ethylenediamine-β-phenethylamine-Boc-protected ethylenediamine-2-(4-

The preparation method of the peptoid macromolecule specifically includes the following steps:
(1) a Rink amide AM resin (starting resin for polypeptide synthesis, the level of substitution was 0.3 mmol/g) was swollen, and then deprotected with hexahydropyridine; and β-phenethylamine was mixed equimolarly with 1-hydroxybenzotriazole and coupled under the activation of N-methylmorpholine;
(2) 25 mL of bromoacetic acid with a concentration of 2 mol/L and 22 mL of N,N'-diisopropylcarbodiimide (DIC) with a concentration of 3.2 mol/L were added into the Rink amide AM resin, and reacted at 38° C. for 30 minutes to acylate the amino group at the end of the resin;
(3) 3 mol/L primary amine was added and reacted at 37° C. for 90 min so as to replace the bromine atom by nucleophilic substitution reaction to complete the synthesis of one subunit;
(4) steps (2) and (3) were repeated until the synthesis of remaining subunits was completed; and
(5) after the synthesis was completed, the side chain protecting group was removed, and the peptoid macromolecule was cleaved from the resin with a cleaving agent including 95 wt % trifluoroacetic acid, 2.5 wt % ultrapure water and 2.5 wt % triisopropylsilane.

For example, in the process of forming the peptoid macromolecule of the above structure, the input order of subunit donors is:

β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-2-(4-biphenylyl)ethylamine-3-aminopropionic acid-β-phenethylamine-3-aminopropionic acid-Boc-protected 1,4-butanediamine-2-(4-biphenylyl)ethylamine-3-aminopropionic acid-β-phenethylamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-3-phenethylamine-Boc-protected ethylenediamine-2-(4-Biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl)ethylamine-Boc-protected ethylenediamine-β-phenethylamine-Boc-protected ethylenediamine-2-(4-biphenylyl) ethylamine-Boc-protected ethylenediamine.

For example, the peptoid macromolecule can be dissolved in a mixed solution of dimethyl sulfoxide (DMSO) and water (H₂O) with a molar ratio of 2:1 (dimethyl sulfoxide: water) to obtain a concentration of 2 mM.

Figure 2:
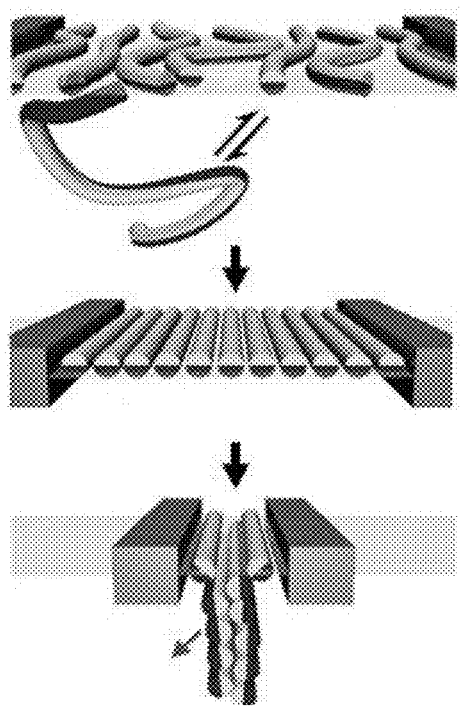
FIG. 2 is a schematic diagram of the formation process of the peptoid nanosheet according to an example disclosed herein.

FIG. 2 is a schematic diagram of the formation process of a two-dimensional peptoid macromolecule provided by an example disclosed herein. The process of forming a two-dimensional peptoid macromolecule is shown in FIG. 2. The peptoid macromolecules provided by the example disclosed herein are placed in a Langmuir trough, wherein the peptoid macromolecules include a hydrophilic end and a hydrophobic end, and in the absence of an external force, the peptoid macromolecules are arranged disorderly at the gas-liquid interface. Then an external force is applied to the disorderly arranged peptoid macromolecules, so that the peptoid macromolecules are arranged in an orderly manner at the gas-liquid interface. An external force is further applied to the orderly arranged peptoid macromolecules, so that the peptoid macromolecules are squeezed below the gas-liquid interface. Below the gas-liquid interface, the hydrophilic end is exposed outside, and the hydrophobic end is inside, thereby forming a two-dimensional structure.

Figure 3A:
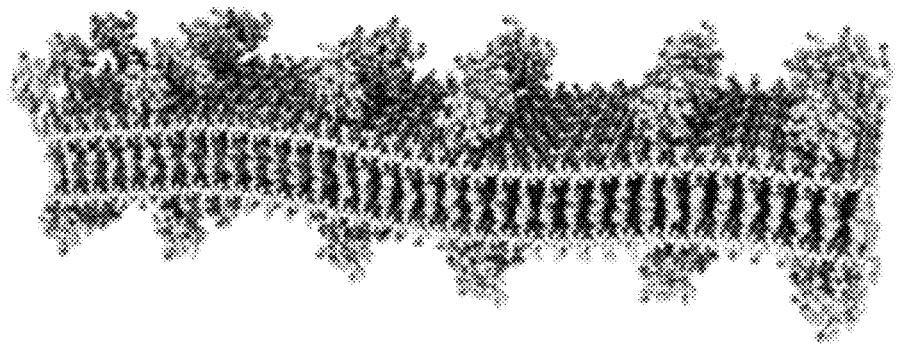
FIG. 3a is a schematic diagram of a structure of the peptoid nanosheet after self-assembly according to an example disclosed herein.
Figure 3B:
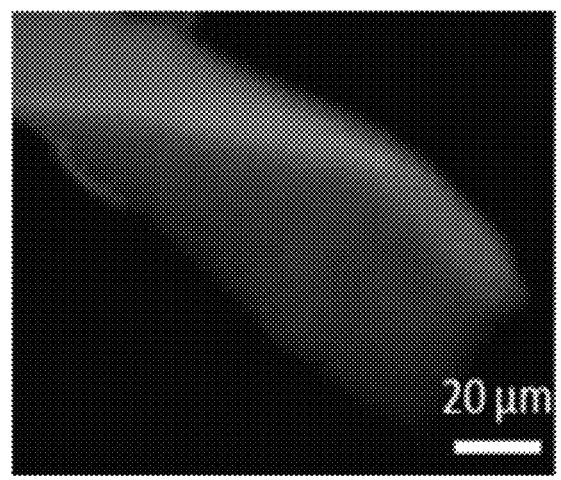
FIG. 3b is a fluorescence microscope characterization diagram of the peptoid nanosheet after self-assembly according to an example disclosed herein.

FIG. 3a is a schematic diagram of forming a nanosheet structure after the self-assembly of peptoid macromolecules. Taking the peptoid compound of Formula IV in Example 1 as an example, the formation process of the nanosheet of peptoid macromolecules is illustrated as follows. The peptoid macromolecules with a concentration of 2 mM is dissolved in a solution of 10 mM 2-[4-(2-hydroxyethyl)piperazin-1-yl]ethanesulfonic acid and 100 mM sodium chloride with a pH of 8.0, and diluted in a buffer for nanosheet formation to a final concentration of 1 to 100 μM, for example, 20 PM. Then a manual shaking method is carried out: storing the peptoid solution stably at room temperature for 22 hours, then gently shaking it manually for 30 seconds, then stabilizing it for 1 minute, and repeating the shaking-stabilization process for 5 times; or a machine shaking method is carried out: slowly rotating the peptoid solution in a tube from horizontal to vertical (0.6 rpm), once every 450 seconds. Nile Red is added to the resulting peptoid solution for nanosheet at a final concentration of 1 μM. The solution is placed on 1% agar, and is observed with a fluorescence microscope (Vert.A1, Carl Zeiss Far East, Germany). The result is shown in FIG. 3b, and a clear nanosheet structure can be observed.

The peptoid compounds provided by the examples disclosed herein have a simple synthesis process and strong binding ability to EpCAM protein. They can effectively screen the serum of health humans and patients with colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma through the EpCAM protein in the serum, thereby specifically identifying the EpCAM protein on the CTC surface of colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma. This provides a favorable guarantee for capturing the corresponding CTC with high sensitivity. For example, molecular probes with high affinity and sensitivity to EpCAM protein can be designed.

For example, the procedures for testing the binding ability of peptoid compounds of Formula I or peptoid macromolecules to EpCAM protein by surface plasmon resonance imaging technology are as follows:
(1) dissolving the peptoid compounds of Formula I or the peptoid macromolecules in ddH₂O to a concentration of 1 to 1000 μM;
(2) spotting the aforementioned solution of the peptoid compounds of Formula I or the peptoid macromolecules on the surface of a 3D chip, repeating 3 points for each kind of sample, and placing the chips at 4° C. for 12 hours; washing the chip with 10×PBS, 1×PBS, and ultrapure water, and then blocking the chip with 1 M aminoethanol hydrochloride for 30 minutes; then washing the chip 5 times with ultrapure water, and finally drying the chip with nitrogen gas;

(3) mounting the chip on the SPRi instrument, measuring the SPRi angle and adjusting it to the best optical position; selecting relevant detection points in the detection area, including sample points and blank points, and setting the flow rate of the test to 2 µL/s; and
(4) selecting PBS as the buffer and passing it into a flow cell until the baseline is stable, and then introducing EpCAM solutions with concentrations of 5.68 nM, 11.4 nM, 22.8 nM, 45.6 nM and 91.2 nM for detection, wherein the binding time is 300 seconds, the dissociation time is 300 seconds, and phosphoric acid is introduced before next concentration for regeneration.

Figure 4A:
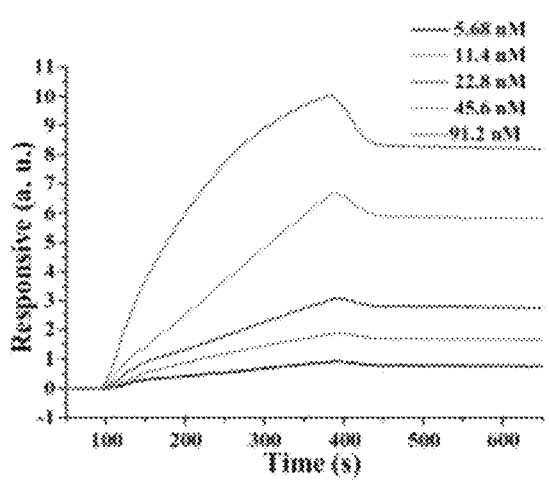
FIG. 4a shows the result of surface plasmon resonance detection of the binding of a peptoid compound of Formula IV according to an example disclosed herein to an EpCAM protein with concentrations of 5.68 nM, 11.4 nM, 22.8 nM, 45.6 nM and 91.2 nM.

FIG. 4a is a graph showing the results of surface plasmon resonance detection of the binding of a peptoid macromolecule of Formula IV disclosed herein to an EpCAM protein with concentrations of 5.68 nM, 11.4 nM, 22.8 nM, 45.6 nM and 91.2 nM, respectively, in which, ΔRU represents the binding signal of the mobile phase after passing through the array minus the baseline signal of the initial PBS buffer, and the curve is the test result of PlexArray HT. The fitted straight line is obtained by BIAevalution 4.1, and ΔRU is used to reflect the intensity of binding signals in surface plasmon resonance imaging and is a dimensionless unit. After fitting, the equilibrium dissociation constant $K_D$ is $2.18 \times 10^{-10}$ mol/L, which indicates that the peptoid macromolecule has a very high level of affinity with EpCAM protein.

Figure 4B:
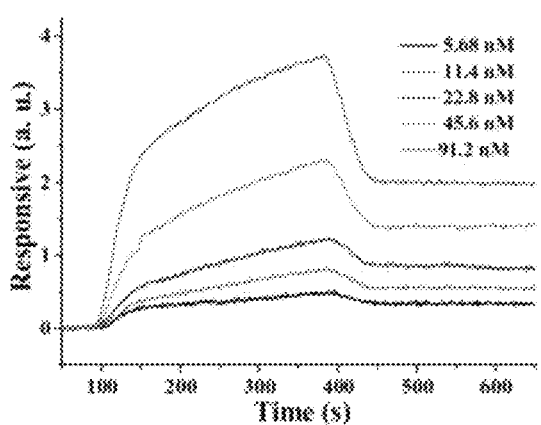
FIG. 4b shows the result of surface plasmon resonance detection of the binding of a peptoid compound of Formula I according to an example disclosed herein to an EpCAM protein with concentrations of 5.68 nM, 11.4 nM, 22.8 nM, 45.6 nM and 91.2 nM.
Figure 5:
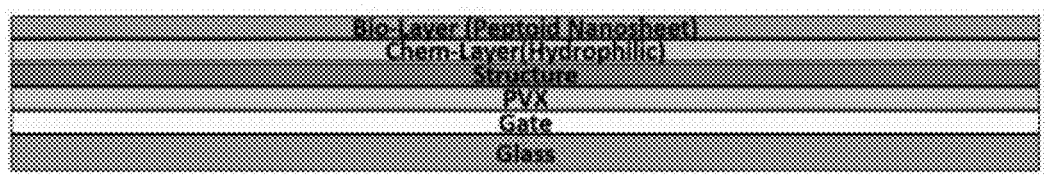
FIG. 5 is a schematic diagram of a structure of a peptoid nanosheet used in a detection chip.

FIG. 4b is a graph showing the results of surface plasmon resonance detection of the binding of a peptoid small molecule of Formula II disclosed herein to an EpCAM protein with concentrations of 5.68 nM, 11.4 nM, 22.8 nM, 45.6 nM and 91.2 nM, respectively. After fitting, the equilibrium dissociation constant $K_D$ is $1.87 \times 10^{-8}$ mol/L.

Compared with the peptoid small molecule of Formula II, the equilibrium dissociation constant of the peptoid macromolecule of Formula IV has been increased from the order of $10^{-8}$ mol/liter to the order of $10^{-10}$ mol/liter. This indicates that the peptoid macromolecules disclosed herein can effectively increase the affinity of molecular probes with target proteins. The peptoid macromolecules disclosed herein can be used for detection in the early stage of onset without causing trauma to the patient, and can effectively reduce non-specific adsorption on the surface of the chip and result in high accuracy and good specificity of detection. In addition, the peptoid macromolecules disclosed herein have simple synthesis and low cost.

The specific steps for detecting the serum of patients with colorectal adenocarcinoma, gastric adenocarcinoma, breast cancer, ovarian cancer, lung adenocarcinoma, prostate cancer, pancreatic cancer, stem cell cancer, retinoblastoma, or primary esophageal squamous cell carcinoma and the serum of health humans by using peptoid macromolecules through surface plasmon resonance imaging technology are as follows:

(1) spotting a solution of peptoid macromolecules on the surface of a 3D chip, repeating 3 points for each kind of sample, and placing the chip at 4° C. for 12 hours; washing the chip with 10×PBS, 1×PBS, and ultrapure water, and then blocking the chip with 1 M aminoethanol hydrochloride for 30 minutes; then washing the chip 5 times with ultrapure water, and finally drying the chip with nitrogen gas; mounting the above chip on the SPRi instrument, measuring the SPRi angle and adjusting it to the best optical position; selecting relevant detection points in the detection area, including sample points and blank points, and setting the flow rate of the test to 2 µL/s; and (2) selecting PBS as the buffer and passing it into a flow cell until the baseline is stable, and then introducing the dilutions (1:5000) of serums from different patients and health humans, wherein the binding time is 300 seconds, the dissociation time is 300 seconds, and phosphoric acid and proteinase K are introduced for regeneration before next sample.

According to the binding strength of peptoid macromolecules with surface plasmon resonance imaging signals, patients with colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma can be distinguished from health humans.

For example, the surface plasmon resonance imaging technology is used to test the sensitivity in detecting serum of the diagnostic system for colorectal adenocarcinoma, gastric adenocarcinoma, breast cancer, ovarian cancer, lung adenocarcinoma, prostate cancer, pancreatic cancer, stem cell cancer, retinoblastoma, or primary esophageal squamous cell carcinoma. The specific steps are as follows:

(1) dissolving peptoid macromolecules in a double distilled water, spotting the solution on the surface of a 3D chip, repeating 3 points for each kind of sample, and placing the chip at 4° C. for 12 hours; washing the chip with 10×PBS, 1×PBS, and ultrapure water, and then blocking the chip with 1 M aminoethanol hydrochloride for 30 minutes; then washing the chip 5 times with ultrapure water, and finally drying the chip with nitrogen gas; mounting the above chip on the SPRi instrument, measuring the SPRi angle and adjusting it to the best optical position; selecting relevant detection points in the detection area, including sample points and blank points, and setting the flow rate of the test to 2 µL/s;

(2) selecting PBS as the buffer and passing it into a flow cell until the baseline is stable, and then introducing the dilutions of serums from different patients and health humans, wherein the dilution concentrations are 1:2000, 1:4000, 1:8000, 1:16000, and 1:32000, respectively, the binding time is 300 seconds, the dissociation time is 300 seconds, and phosphoric acid and proteinase K are introduced for regeneration before next sample.

The test results show that when the dilution ratio of serum is less than or equal to 1:8000, patients with colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma with high EpCAM expression can be clearly distinguished from health humans, demonstrating its extremely high sensitivity.

For example, the chip is a PlexArray HT 3D chip purchased from Plexera Bioscience Inc., USA.

For example, the peptoid macromolecules self-assemble at the gas-liquid interface to form a nanosheet having on the surface a peptoid that specifically identifies EpCAM protein. The peptoid nanosheet serves as a scaffold to exhibit and support the peptoid as a molecular probe to identify EpCAM protein. The peptoid nanosheet combined with surface plasmon resonance technology can be used for the detection of colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma.

For example, the peptoid macromolecules are a two-dimensional nanosheet material, so that the peptoid macromolecules can be coupled to a sensor, and the peptoid compounds with affinity can be exhibited on the surface of the sensor.

At least one example disclosed herein also provides a detection chip, wherein any one of the aforementioned peptoid compounds is coupled to the surface of the chip. For example, the surface of the detection chip is coupled with any of the aforementioned peptoid macromolecules, preferably the peptoid macromolecule of Formula IV. For example, FIG. 6 shows that a peptoid nanosheet is coupled to the surface of the detection chip to form a biological layer, which is located on the hydrophilic chemical layer.

For example, the aforementioned detection chip may be a microfluidic chip.

For example, the microfluidic chip includes a microvalve control layer and a microvalve film layer. The microvalve control layer is provided with three gas channels, as well as six holes through the control layer. The three holes are sample loading holes, which are communicated with a substrate and used for inflow and outflow of samples and reagents; and the other three holes are connected to the three gas channels, respectively, for gas injection and to control the opening and closing of microvalve. The microvalve film layer is provided with three holes through the film layer, which are communicated with the three sample loading holes of the above-mentioned microvalve control layer, respectively.

For example, the outline dimensions of the microvalve control layer and the microvalve film layer should match the substrate.

The peptoid compounds disclosed herein can also be labeled with a fluorescent molecule. The type of fluorophore is not particularly limited, as long as the modification can impart fluorescent properties to the peptoid compound and the modified peptoid compound can also realize the basic function of the peptoid compound. The peptoid compounds disclosed herein can be modified with one or more fluorophores. For example, a single fluorescently labeled peptoid compound is obtained by modification with one fluorophore, or a double fluorescently labeled peptoid compound is obtained by modification with two fluorophores. In some embodiments, the fluorophore may be selected from, without limitation, blue fluorescent dyes, near-infrared fluorescent dyes, green fluorescent dyes, and the like, e.g. coumarin-containing fluorophores, anthracene-containing fluorophores, rhodamine fluorophores, phenanthrenoimidazole fluorophores, naphthalene-containing fluorophores, fluorescein isothiocyanate, carboxyfluorescein (FAM), fluorescein thiocyanate (FITC), dansyl chloride, 2,4-dinitrophenylhydrazine (Dnp), carboxyrhodamine 110, Texas Red, pentamethine cyanine dyes (Cy5), heptamethine cyanine dyes (Cy7), etc.

The above detection chip can be useful in detecting or diagnosing a disease associated with EpCAM protein. For example, the disease is colorectal adenocarcinoma, gastric adenocarcinoma, breast cancer, ovarian cancer, lung adenocarcinoma, prostate cancer, pancreatic cancer, stem cell cancer, retinoblastoma or primary esophageal squamous cell carcinoma.

In the case of no conflict, the embodiments disclosed herein and the features in the embodiments can be combined with each other to obtain new embodiments. The protection scope of the present invention is not limited to the aforementioned embodiments, and should be defined by the claims.

What is claimed is:

1. A peptoid compound comprising a structure as shown in Formula I,

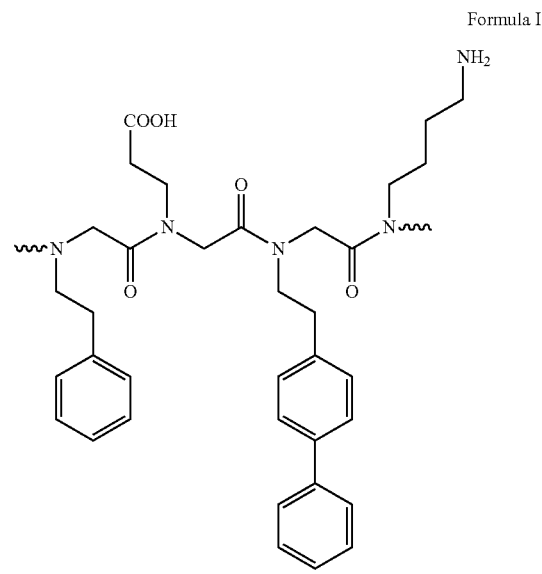

Formula I wherein the peptoid compound includes a 1,4-butanediamine subunit, a 2-(4-biphenylyl)ethylamine subunit, a 3-aminopropionic acid subunit and a phenethylamine subunit.

2. The peptoid compound according to claim 1, having a molecular structural formula of:

Formula II

3. The peptoid compound according to claim 1, wherein a total number of the 1,4-butanediamine subunit, the 2-(4-biphenylyl)ethylamine subunit, the 3-aminopropionic acid subunit and the phenethylamine subunit is 30 to 100.

4. The peptoid compound according to claim 1, wherein the structure as shown in Formula I is not located at the two ends of the structure of the peptoid compound.

5. The peptoid compound according to claim 4, having a molecular structural formula of:

Formula III
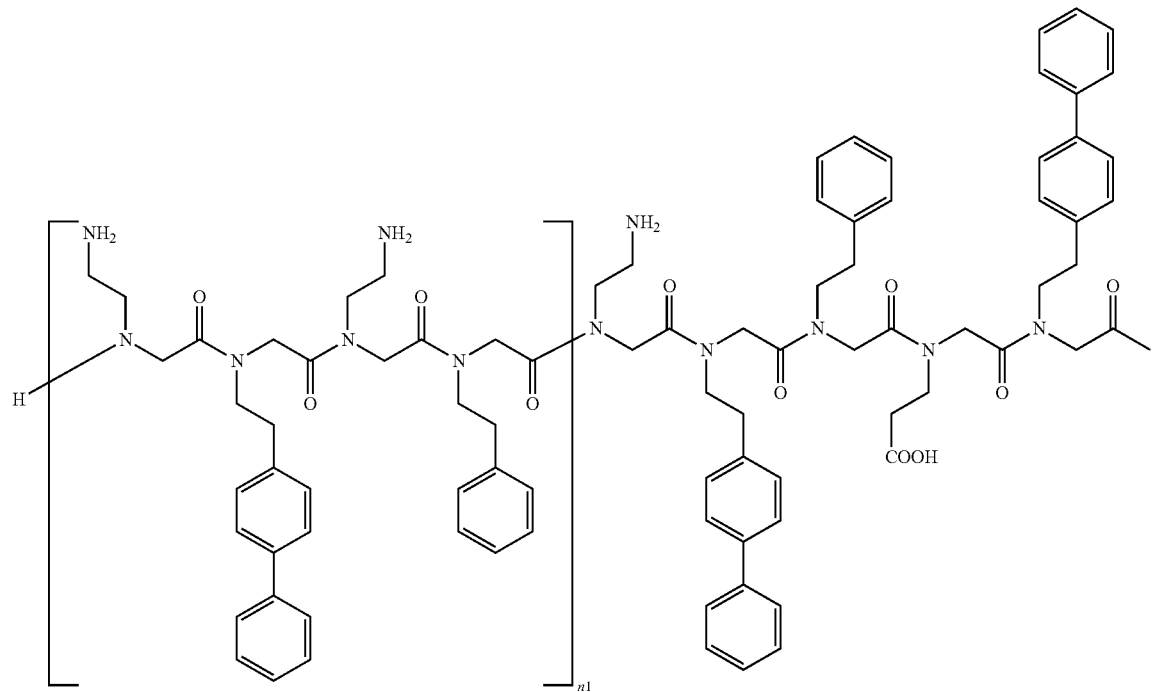
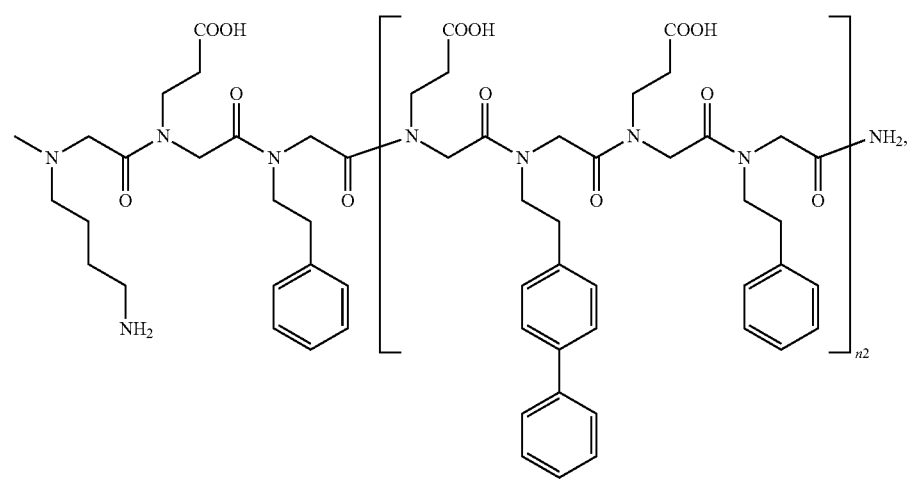
wherein n1 is greater than or equal to 3 and less than or equal to 10; n2 is greater than or equal to 3 and less than or equal to 10; and n1 and n2 are both natural numbers.

6. The peptoid compound according to claim 5, wherein n1 is equal to n2.

7. The peptoid compound according to claim 6, wherein n1 is 3, 5 or 7.

8. The peptoid compound according to claim 7, having a molecular structural formula of:

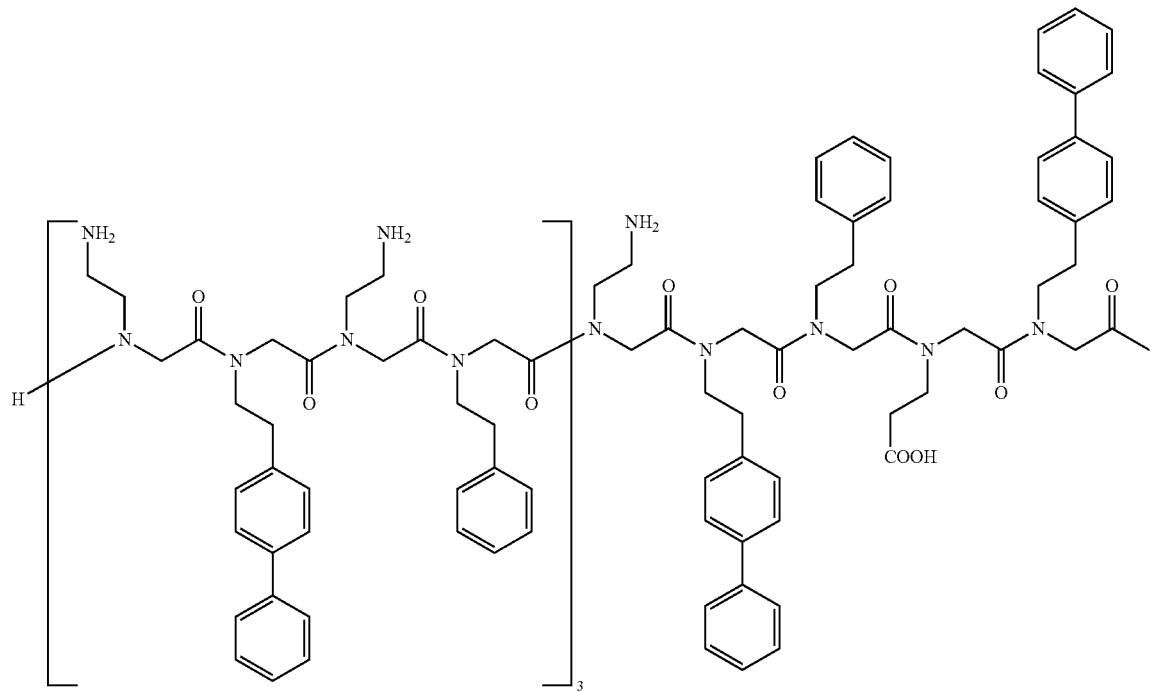

Formula IV

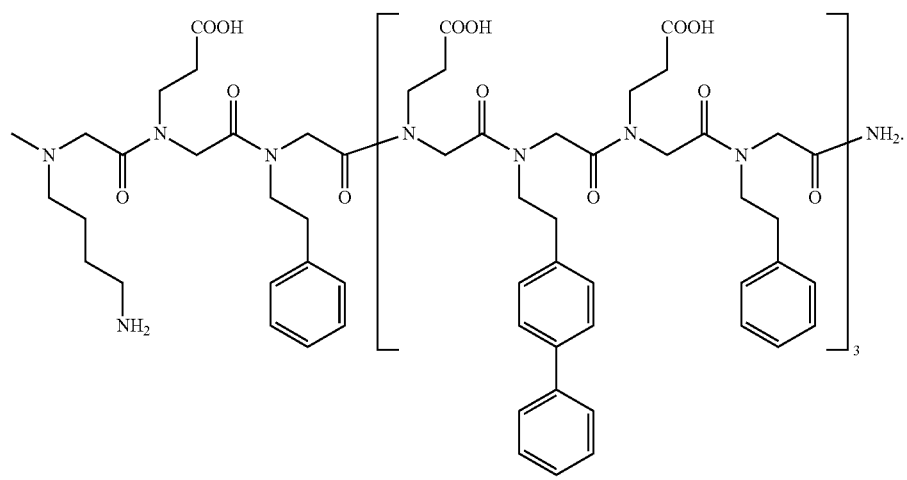

9. A detection chip, wherein a peptoid compound is coupled to a surface of the chip, the peptoid compound includes a 1,4-butanediamine subunit, a 2-(4-biphenylyl) ethylamine subunit, a 3-aminopropionic acid subunit and a phenethylamine subunit, and the peptoid compound includes a structure as shown in Formula I, Formula I
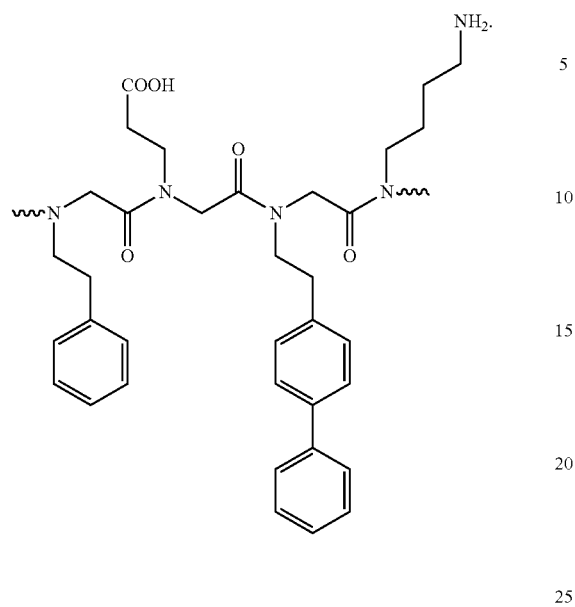
10. The detection chip according to claim 9, wherein the peptoid compound coupled to the surface of the chip is a peptoid compound of
Formula IV
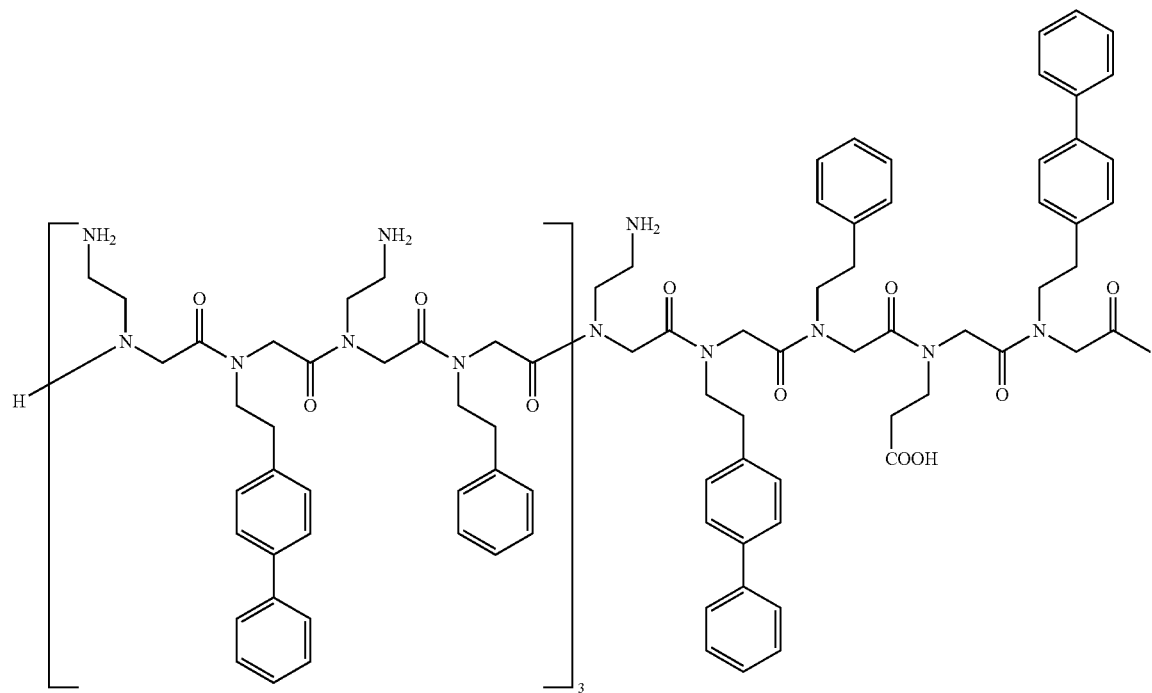

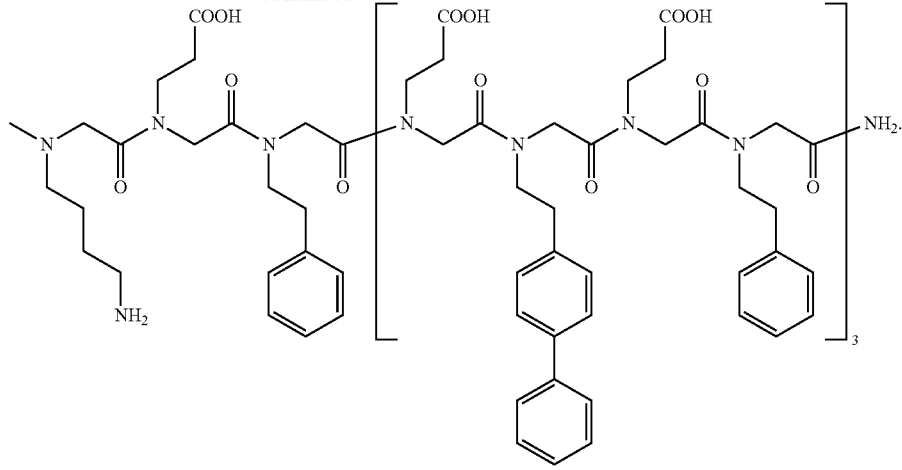

11. The detection chip according to claim 9, which is a microfluidic chip.

12. The detection chip according to claim 9, wherein the chip is useful in detecting or diagnosing a disease associated with Epithelial cell adhesion molecule (EpCAM) protein.

13. The detection chip according to claim 12, wherein the disease is associated with EpCAM protein.

14. The detection chip according to claim 9, wherein the peptoid compound coupled to the surface of the chip is a peptoid compound of

15. The detection chip according to claim 9, wherein a total number of the 1,4-butanediamine subunit, the 2-(4-biphenylyl)ethylamine subunit, the 3-aminopropionic acid subunit and the phenethylamine subunit is 30 to 100.

16. The detection chip according to claim 9, wherein the structure as shown in Formula I is not located at the two ends of the peptoid compound coupled to the surface of the chip

17. The detection chip according to claim 16, wherein the peptoid compound coupled to the surface of the chip comprises a molecular structural formula of:

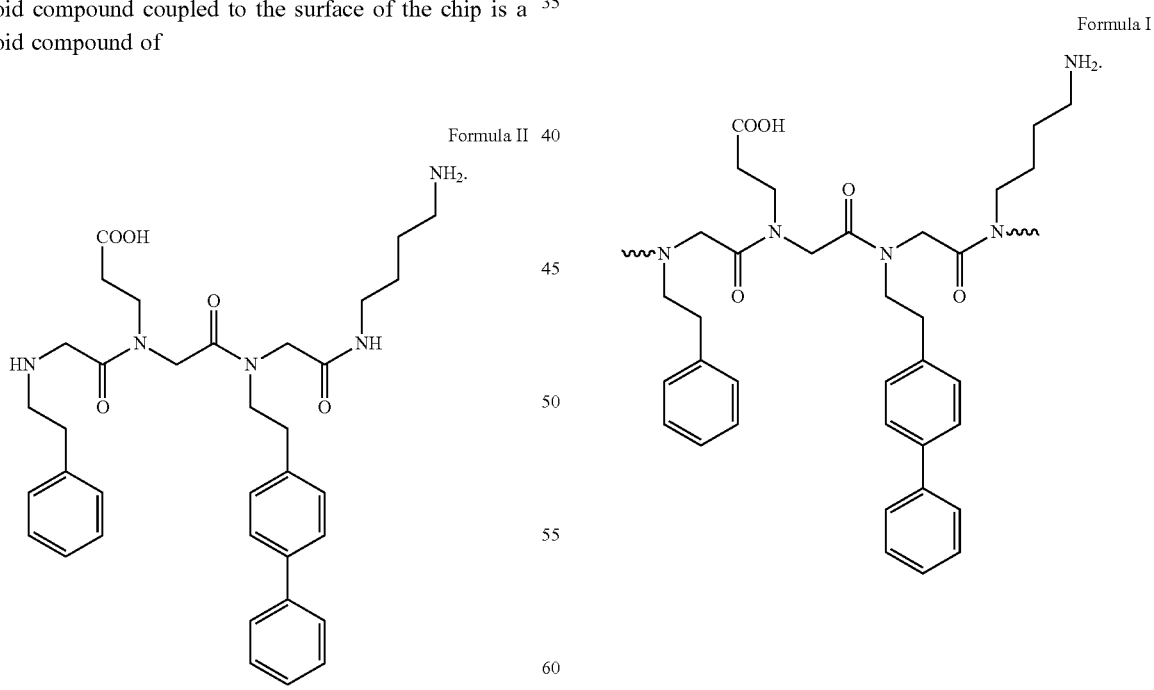

Formula III
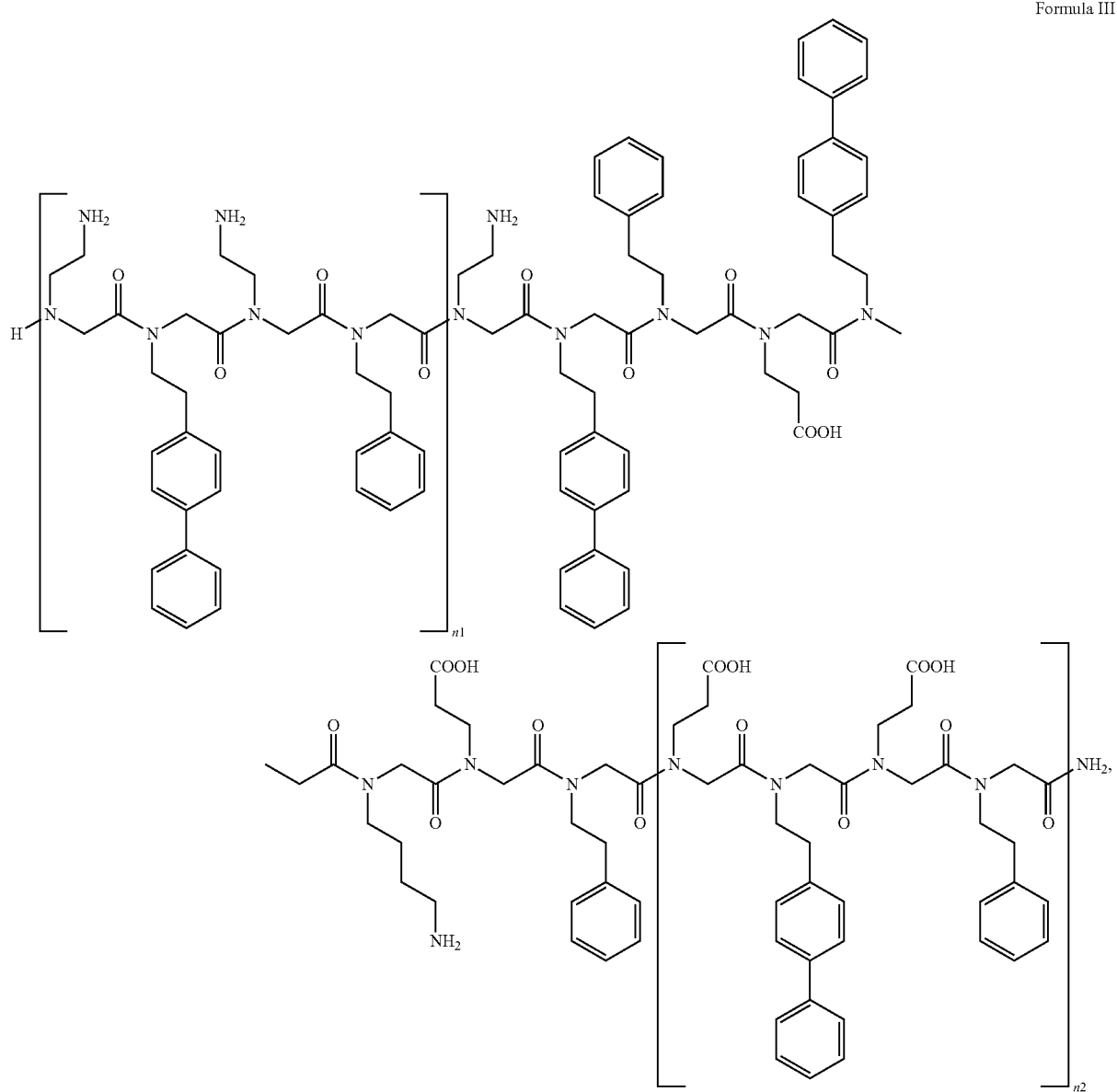
wherein n1 is greater than or equal to 3 and less than or equal to 10; n2 is greater than or equal to 3 and less than or equal to 10; and n1 and n2 are both natural numbers.
18. The detection chip according to claim 17, wherein n1 is equal to n2.
19. The detection chip according to claim 18, wherein n1 is 3, 5 or 7.
* * * * *